United States Patent
Cirrito et al.

(10) Patent No.: US 11,035,863 B2
(45) Date of Patent: Jun. 15, 2021

(54) METHODS FOR ALLERGY DIAGNOSIS

(71) Applicant: IMMUNOVENT, LLC, New York, NY (US)

(72) Inventors: Thomas P. Cirrito, Long Island City, NY (US); Kate M. Rochlin, New York, NC (US)

(73) Assignee: IMMUNOVENT, LLC, New York, NY (US)

( * ) Notice: Subject to any disclaimer, the term of this patent is extended or adjusted under 35 U.S.C. 154(b) by 382 days.

(21) Appl. No.: 15/544,944

(22) PCT Filed: Jan. 21, 2016

(86) PCT No.: PCT/US2016/014265
§ 371 (c)(1),
(2) Date: Feb. 2, 2018

(87) PCT Pub. No.: WO2016/118713
PCT Pub. Date: Jul. 28, 2016

(65) Prior Publication Data
US 2018/0011108 A1 Jan. 11, 2018

Related U.S. Application Data
(60) Provisional application No. 62/106,495, filed on Jan. 22, 2015.

(51) Int. Cl.
*G01N 33/68* (2006.01)
*G01N 33/53* (2006.01)
*C07K 16/42* (2006.01)

(52) U.S. Cl.
CPC ..... *G01N 33/6854* (2013.01); *C07K 16/4291* (2013.01); *G01N 33/5306* (2013.01); *C07K 2318/20* (2013.01); *G01N 2800/24* (2013.01)

(58) Field of Classification Search
None
See application file for complete search history.

(56) References Cited

U.S. PATENT DOCUMENTS

2011/0071043 A1  3/2011  Sampson et al.
2011/0151477 A1  6/2011  Reisacher

OTHER PUBLICATIONS

Baumann,M. J., Eggel, A., Amstutz, P., Stadler, B. M. & Vogel,M. DARPins against a functional IgE epitope. Immunol. Lett. 133, 78-84 (2010).*
Eggel, A., Baumann, M. J., Amstutz, P., Stadler, B. M. & Vogel, M. DARPins as bispecific receptor antagonists analyzed forimmunoglobulin E receptor blockage. J. Mol. Biol. 393, 598-607 (2009).*
Pluckthun et al. 'Designed Ankyrin Repeat Proteins (DARPins): Binding Proteins for Research, Diagnostics, and Therapy.' Annu. Rev. Pharmacol. Toxicol. 55:489-511, 2015.*
Atta et al., "Anti-Leishmanial IgE Antibodies: A Marker of Active Disease in Visceral Leishmaniasis," Am. J. Trop. Med. Hyg., vol. 59, No. 3 (1998); pp. 426-430.
Gould et al., IgE in allergy and asthma today, Nature Reviews | Immunology, vol. 8, Mar. 2008; pp. 205-217.
Kim et al., "Accelerated Disassembly of IgE: Receptor Complexes by a Disruptive Macromolecular Inhibitor," Nature, Nov. 22, 2012; 491 (7425); pp. 613-617.
Mathur et al., "Immunolglobulin E levels and antisperm antibody titers in infertile couples," Am. J. Obstet. Gynecol., vol. 140, No. 8, Aug. 15, 1981; pp. 923-930.
Reisacher, "Mucosal brush biopsy testing of the inferior turbinate to detect local, antigen-specific immunoglobulin E," International Forum of Allergy & Rhinology, vol. 2, No. 1, Jan./Feb. 2012; pp. 69-74.
Smith-Norowitz, et al., "Long Term Persistence of IgE Anti-Influenza Virus Antibodies in Pediatric and Adult Serum Post Vaccination with Influenza Virus Vaccine," Int. J. Med. Sci, vol. 8, No. 3, (2011); pp. 239-244.
Turner et al., "Allergen-specific IgE and IgG4 are markers of resistance and susceptibility in a human intestinal nematode infection," Microbes and Infection, vol. 7, (2005); pp. 990-996.
Youssef et al., "Roles for the High Affinity IgE Receptor, FcERI, of Human Basophils in the Pathogenesis and Therapy of Allergic Asthma: Disease Promotion, Protection or Both?" Open Allergy J., vol. 3, (2010); pp. 91-101.
Eggel et al., "Accelerated dissociation of IgE: FcERI complexes by disruptive inhibitors actively desensitizes allergic effector cells," J. Allergy Clin Immunol., vol. 133, No. 6, Jun. 2014; pp. 1709-1719.
Nikolac, "Lipemia: causes, interference mechanisms, detection and management," Biochemia Medica (2014), vol. 24, No. 1; pp. 57-67.
Binz et al., "Designing Repeat Proteins: Well-expressed, Soluble and Stable Proteins from Combinatorial Libraries of Consensus Ankyrin Repeat Proteins," J. Mol. Biol. (2003); vol. 332; pp. 489-503.
European search report dated Aug. 28, 2018, corresponding to counterpart European Application No. 16740734.5; 11 total pages.
International Search Report dated Jun. 2, 2016, corresponding to counterpart International Application No. PCT/US16/14265; 3 pages.

(Continued)

*Primary Examiner* — Nora M Rooney
(74) *Attorney, Agent, or Firm* — Carter, DeLuca & Farrell LLP

(57) ABSTRACT

Provided herein are improved methods for diagnosing allergy in a subject using designed ankyrin repeat proteins ("DARPins"), and kits for use in such methods. Also provided herein are novel DARPins and methods of use thereof.

19 Claims, 1 Drawing Sheet
Specification includes a Sequence Listing.

(56) References Cited

OTHER PUBLICATIONS

Conroy et al., "Measurement of IgE on Human Basophils: Relation to Serum IgE and Anti-IgE-Induced Histamine Release," The Journal of Immunology, vol. 118, No. 4, Apr. 1977; pp. 1317-1321.
Eggel et al., "Inhibition of ongoing allergic relations using a novel anti-IgE DARPin-Fc fusion protein," Allergy, vol. 66, (2011); pp. 961-968.
Dehlink et al., "Relationships between Levels of Serum IgE, Cell-Bound IgE, and IgE-Receptors on Peripheral Blood Cells in a Pediatric Population," PLoS ONE, vol. 5, Issue 8, e12204, (Aug. 2010); pp. 1-6.
European Examination Report dated Jun. 25, 2019 issued in corresponding EP Appln. No. 16 740 734.5-1116.

* cited by examiner

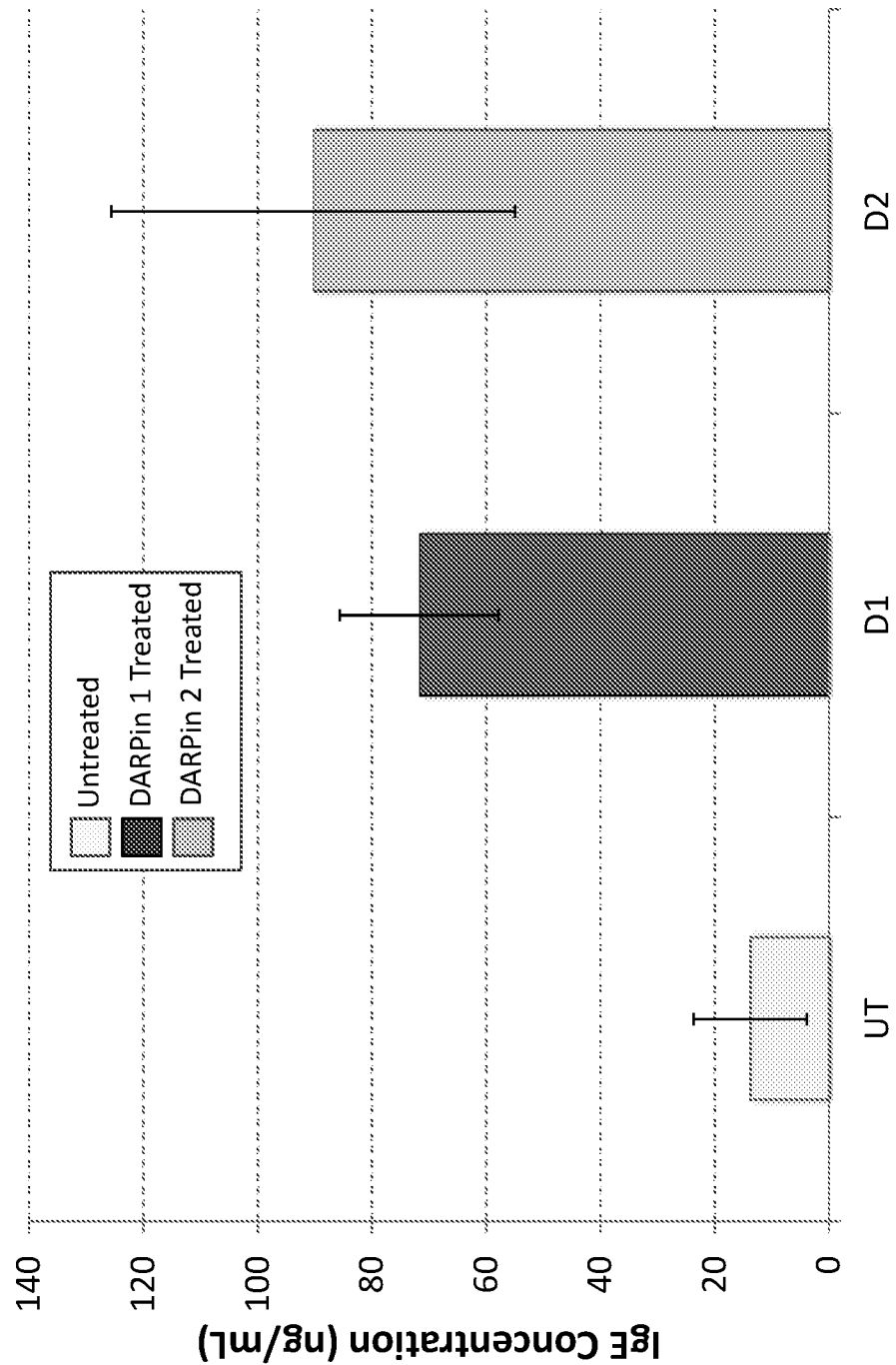

METHODS FOR ALLERGY DIAGNOSIS

This application is a national stage entry of International Patent Application No. PCT/US2016/014265, filed Jan. 21, 2016, which claims to the benefit of U.S. Provisional Patent Application No. 62/106,495, filed Jan. 22, 2015, the disclosures of each of which are incorporated herein by reference in their entireties.

1. FIELD

Provided herein are improved methods for diagnosing allergy in a subject using designed ankyrin repeat proteins ("DARPins"), and kits for use in such methods. Also provided herein are novel DARPins and methods of use thereof.

2. BACKGROUND

Allergy symptoms primarily manifest in the mouth and nasal cavity, where initial exposure to an allergen is most likely to occur. Allergy is caused by the degranulation of mast cells and basophils, e.g., in the nasopharynx, as a result of exposure to an allergen in the presence of allergen-specific immunoglobulin E (IgE). IgE is unique among the immunoglobulins in that affinity of IgE for the high affinity IgE receptor (Fcε-R1 or Fcε R1) is very high, and because IgE can bind via its Fc portion to the high affinity receptor in the absence of its specific allergen. As a result, resident basophils and mast cells, e.g., in the nasopharyx, which express high levels of Fcε-R1, are pre-loaded with IgE. Upon exposure to an allergen to which a subject is sensitized (meaning there is already allergen-specific IgE present), the allergen binds to the cell-bound IgE and cross links the Fcε-R1, resulting in a signal to the cell to degranulate. Due to the "pre-loaded" nature of mast cells and basophils, degranulation happens very quickly after exposure to an allergen, resulting in the immediate onset of symptoms of allergy, which can be life threatening.

Skin tests (e.g., the skin prick test), blood tests (e.g., the radioallergosorbent test (RAST), food challenge, and nasal provocation represent the primary means by which subjects are tested for allergy.

Skin tests require introduction of small amounts of allergen to a subject's skin. Allergen can be introduced by pricking the skin with a needle (or multiple needles) coated with allergen (the skin prick test), by scratching or scraping the skin with an object (e.g., a lancet) covered with allergen (the skin scratch and skin scrape tests, respectively), using a patch covered by allergen (the patch test), or by injection of an allergen under the dermis of the skin (the intradermic test). Following introduction of allergen, skin is monitored for, e.g., redness and swelling, rash, and/or urticaria (hives). Allergic reactions typically will manifest as a "skin wheal," which is a visually apparent spot (red and/or puffy appearance) of inflammation on the skin. The diameter of the skin wheal bears some relationship to the severity of the patient's allergy. Typically a skin wheal of 3 mm or greater is indicative of a possible allergic reaction, while skin wheals of less than 3 mm are not considered reliable indicators of allergy. Skin tests can be problematic in that they can cause painful and/or itchy rashes, or can lead to more dangerous conditions, such as anaphylaxis. Further, skin testing is contraindicated for subjects of certain ages and subjects taking certain medications as well as providing variable results based on the physician technique or quality of the extracts.

Blood tests measure allergen-specific levels of IgE in the circulation of a subject. IgE detected in blood is generally solubilized IgE that is not bound to an IgE cell receptor, such as those found on some epithelial cells and lymphocytes. These tests require that blood be drawn and laboratory analyzed using ELISA or allergen array technology.

Food challenge testing involves feeding a patient a suspected allergy triggering food in measured doses, starting with very small amounts that are unlikely to trigger symptoms. Following each dose, the patient is observed for a period of time for signs of a reaction. Doses are gradually increased until a reaction is noted or, if no reaction emerges, the suspected food is eliminated as a potential allergy trigger. Likewise with nasal challenge testing, measured doses of a single suspected allergen are placed in the nasal passage (inferior and middle turbinate areas) of a patient, with a ~15 minute period of observation for emerging symptoms. If no symptoms emerge, the process is repeated with the same allergen at escalating dose until a reaction is achieved or until the allergen can be eliminated as a causative agent. Challenge testing (e.g., with food and nasal allergens) should only be carried out with a limited number of positive reactions in each session (e.g., per day), as a positive allergic reaction in a patient should be given time to subside before additional allergen tests can be administered. Thus, there are practical limitations on the number of allergens that can be tested with such challenge tests.

Neither skin testing nor blood testing can be used to detect allergies at the relevant location of an allergic reaction, and therefore do not allow for allergy IgE testing (e.g., testing at the reaction site, such as the mouth, nose, sinus, throat, or stomach). Further, current allergy testing methods, including blood and skin tests, are deficient because levels of antigen-specific IgE in the blood and/or skin are sometimes not high enough to make accurate diagnoses of allergy. Indeed, it is known that some allergy patients do not have any distal IgE circulating in serum or available in the epidermis and, accordingly, cannot be reliably diagnosed with current blood and skin testing methods.

While oral and nasal challenges do monitor inflammatory processes at the location of allergic reaction, they remain indirect measurements of IgE levels and, as such, are difficult to standardize. Moreover, challenge testing is time consuming and has the additional emotional and clinical risk of directly exposing the patient to allergens that may cause severe inflammatory reactions.

There remains a need in the art for rapid, accurate, local, non-invasive, and non-harmful methods of allergy testing. Such methods are provided herein.

3. SUMMARY

Allergen/antigen-specific IgE exists in tissues involved in the allergic response in subjects. For example, allergen/antigen-specific IgE can be found in the epithelium of the nose and mouth of subjects. See, e.g., Reisacher, 2012, Int. Forum Allergy Rhinol. 2(1):69-74. However, use of the IgE from cells that make up the epithelium in allergy testing is limited because the IgE associated with the cells binds its receptor on the cells with such high affinity that isolation and concentration of sufficient amounts of IgE for analysis is difficult. Indeed, IgE binds to its specific "high-affinity IgE receptor" (also referred to as the Fcε-R1 receptor) on basophils and mast cells with extremely high affinity (kd approximately $10^{-10}$ M) such that the estimated half-life of the IgE/Fcε-R1 complex in vivo is 10 days or more (see, e.g., Youssef et al., 2010, The Open Allergy Journal, 3:91-101;

Gould and Sutton, 2008, Nature Reviews: Immunology, 8:205-217). Accordingly, current allergy tests rely on isolation of blood from subjects or superficial introduction of allergens to subjects (e.g., introduction to the skin).

Designed ankyrin repeat proteins ("DARPins") have been shown capable of dissociating IgE from its high-affinity receptor (see, e.g., Kim et al., 2012, Nature 491:613-617) and have been proposed for use in allergy therapy (see, e.g., Eggel et al., 2014, J. Allergy Clin. Immunol. 133(6):1709-1719). The inventors have discovered that in addition to therapeutic use, DARPins can be used in methods of allergy diagnosis. In particular, the inventors have discovered that DARPins can be used to dissociate allergen/antigen-specific IgE from its receptor on cells found in tissues of subjects (e.g., cells of the epithelium in the mouth and/or nose of subjects, including basophils, mast cells, epithelial cells, and lymphocytes) and that the dissociated IgE can be isolated and tested to determine the allergy profile of the subjects.

In a simplified method, the invention encompasses sampling of cells from a patient's area of allergic reaction, particularly cells from the nasal passages, from the oral cavity, or from the GI tract. The cells are then contacted with a preparation of DARPin proteins to release all IgEs from their high-affinity cells receptors. The resulting sample will then contain solubilized, freely accessible IgEs that can be tested for the presence of various specific IgEs, via an immunoassay, that can indicate a specific allergy in the patient. Therefore, in one aspect, provided herein are novel methods for determining the allergy profile of subjects, wherein such methods can be performed using tissue directly involved in allergic reactions, or in tissue samples derived directly from sites of allergic reaction and inflammation.

The methods described herein are non-invasive (epithelial cells of, e.g., the nose and/or mouth, can be obtained by mucosal brush biopsy) and non-harmful (no allergens are introduced to the subject when practicing the methods. The methods provided herein can be used to determine the systemic presence and levels of specific allergy markers, namely IgE with specificity to a known allergen. Accordingly, the test allows for determination of specific allergies giving rise to allergy symptoms in subjects by collecting and processing a sample of cells from a mucosal brush biopsy. Thus the methods provided herein can, in certain embodiments, be performed on subjects exhibiting symptoms of an allergic reaction (e.g., inflammation), which allows for determination of the specific allergen that is giving rise to the reaction in a subject.

Further, the methods provided herein can be used to determine local presence and levels of specific allergy markers, i.e., IgE with specificity to a known allergen, at the site of allergic symptoms and inflammation (e.g., in the mouth, nose, sinus, esophagus) from a mucosal brush biopsy cell sample. This information, in turn, allows for determination of the specific allergen giving rise to allergy symptoms in subjects at the symptomatic site where the cells were collected with a mucosal brush biopsy (e.g., in the throat, nose, mouth, etc.). Accordingly, the methods provided herein can, in certain embodiments, be performed on subjects exhibiting symptoms of an allergic reaction (e.g., inflammation) at the site of the reaction, thus allowing for determination of the specific allergen giving rise to the local allergy reaction.

In one embodiment, provided herein is a method for diagnosing allergy in a subject, e.g., a human subject, comprising (i) obtaining epithelial cells from a tissue of the subject; (ii) contacting the epithelial cells with a composition comprising one or more DARPins capable of causing IgE to dissociate from its receptor (e.g., Fcε-R1); (iii) isolating the dissociated IgE; and (iv) determining the allergen specificity or specificities of the IgE. In a specific embodiment, said epithelial cells are isolated from the mouth, nose, sublingual space, buccal cavity, esophagus, and/or sinus cavity of the subject. In another specific embodiment, said DARPin comprises one or more of SEQ ID NOs. 1-16, or a sequence with about or at least 85% homology, about or at least 90% homology, about or at least 95% homology, or about or at least 98% homology to any one of SEQ ID NOs. 1-16. In another specific embodiment, said cells are contacted with a solubilization buffer. A solubilization buffer may comprise buffer elements such as HEPES, PBS, TBS, TRIS, Ringer's solution, or IgE-free serum. In certain embodiments, a solubilization buffer may comprise one or more surfactant or detergent agents that can help disrupt cellular membranes such as SDS, Tween 20, Brij 35, Brij 96, Brij 97, Triton X-100, NP-40, or CHAPS. Additionally, in certain embodiments, a solubilization buffer may comprise one or more enzymes that can help disrupt cell-cell contacts such as collagenase, collagenase II, Trypsin, Papain, EDTA, and hyaluronidase. Such a solubilization buffer is designed to support disruption of cell-cell contacts and/or disruption of individual cellular membranes prior to, or simultaneously with, the period in which they are contacted with said DARPin compositions. The dissociated IgE can be measured using methods known to one of skill in the art, e.g., using a fluorescence-based assay (e.g., ELISA), an ImmunoCap (ThermoFisher) or similar IgE detection protocol, or by microarray.

In another embodiment, provided herein is a method for diagnosing allergy in a subject, e.g., a human subject, comprising (i) obtaining epithelial cells from a tissue of the subject; (ii) contacted said cells with a solubilization buffer capable of disrupting the cell membranes; (iii) contacting the resultant composition (i.e., the composition comprising the solubilization buffer/disrupted cells) with a composition comprising one or more DARPins capable of causing IgE to dissociate from its receptor (e.g., Fcε-R1); (iv) isolating the dissociated IgE; and (v) determining the allergen specificity of the IgE. In a specific embodiment, said epithelial cells are isolated from the mouth, nose, sublingual space, buccal cavity, esophagus, and/or sinus cavity of the subject. In another specific embodiment, the isolated epithelial cells are contacted with a solution containing 200 nM-1000 nM of one or more DARPins for 10-40 minutes at room temperature. In another specific embodiment, the one or more DARPins used comprise one or more of SEQ ID NOs. 1-16. The dissociated IgE can be measured using methods known to one of skill in the art, e.g., using a fluorescence-based assay (e.g., ELISA) or by microarray.

In a specific embodiment, a method for diagnosing allergy in a subject provided herein is performed on a subject that has not previously received an allergy test, i.e., the method is performed as a primary diagnostic test. In another specific embodiment, a method for diagnosing allergy in a subject provided herein is performed on a subject that has already received an allergy test, i.e., the method is performed as a secondary diagnostic test to support or additionally clarify a blood or skin test that was inconclusive or inconsistent with the subject's clinical allergy symptoms.

It is known that abnormal levels of lipids (lipemia) in a subject's blood can hinder immunoassays on serum samples for detecting various biomarkers specific IgE in the serum (including ELISAs). Abnormally high levels of lipids from diet, pharmaceutical effects, genetic predisposition, or a combination of these factors, can degrade the accuracy of blood-based biomarker tests that are based on immunoassays (see, e.g., Nikolac, N. Biochem Med (Zagreb). February 2014; 24(1):57-67; and www.questdiagnostics.com/home/physicians/testing-services/specialists/hospitals-lab-staff/specimen-handling/serum-plasma-whole-blood.html). Accordingly, in a further specific embodiment, a method for diagnosing an allergy in a subject is provided herein is performed on a subject who has inaccurate or inconclusive allergy blood test results due to abnormal levels of lipids in the subject's blood.

In certain embodiments, the methods for diagnosing allergy in a subject provided herein can be used to identify an allergy profile of a subject, e.g., to identify most or all of the allergens the subject is allergic to and, conversely, the most or all of the allergens the subject is not allergic to. Comprehensive methods for measuring the allergen-specific profile of IgE are known in the art, e.g., microarray, ImmunoCAP (Thermofisher), and ELISA.

In certain embodiments, the methods for diagnosing allergy in a subject provided herein can be used to determine whether a subject is allergic to a particular allergen of interest. That is, the methods can be used, in combination with an appropriate medical evaluation, to obtain a simple answer of "yes" or "no" with respect to whether or not a subject has a given allergy, e.g., an allergy to peanuts. In other embodiments, the methods provided herein are able to indicate how substantial one or more particular allergies are in a patient, i.e., the methods can stratify patients based on severity of their particular allergies, which is important for determining subsequent disease management and treatment steps. In accordance with such embodiments, assays (e.g., ELISA) can be used to measure whether IgE isolated from the cells of the subject is specific to the allergen of interest.

The methods for diagnosing one or more IgE-mediated allergies in a subject provided herein can be used to identify any type of allergy a subject may be disposed to. In a specific embodiment, the methods for diagnosing allergy in a subject provided herein are used to determine whether or not the subject has a food allergy, e.g., an allergy to peanuts. In another specific embodiment, the methods for diagnosing allergy in a subject provided herein are used to determine whether or not the subject has a seasonal airborne allergy, e.g., an airborne allergy that appears annually during a certain time of each year, such as a tree or grass whose pollen release into the environment peaks on a seasonal cycle. In another specific embodiment, the methods for diagnosing allergy in a subject provided herein are used to determine whether or not the subject has a year-round (perennial) airborne allergy to triggers that the subject is exposed to throughout the year, such as dust mites, cockroaches, cats, and dogs. In a further specific embodiment, the methods for diagnosing allergy in a subject provided herein can be used to determine if a subject has an allergy to a specific stinging insect other venomous or stinging animal.

In further embodiments, the methods for diagnosing one or more IgE-mediated allergies in a subject provided herein can be used to identify any allergy for which there is an available allergen to use as a reagent in the immunoassays which detect and quantitate the sample specific IgEs of the instant invention. Many of such allergens are available and are known in the art. A non-limiting list of allergens that can be used in accordance with the method described herein is presented in Section 4.4, below.

As discussed above, the methods for allergy diagnosis provided herein allow for highly specific identification of local, specific IgEs in subjects, i.e., allergens that are the cause of specific symptoms/reactions identified in the subject. Accordingly, in another aspect, the methods for allergy diagnosis provided herein can be used to identify an insulting allergen, or combination of insulting allergens in a subject, and the subject then can be treated in a manner that results in tolerization of (desensitization to) the insulting allergen/allergens by the subject. For example, tolerance to an allergen/antigen can be achieved in a subject by exposing the subject to the allergen/antigen on a regular basis for a specified time period is sustained for at least two to six months, and, optimally, is sustained for at least 3-5 years. Other immunotherapies are known to generate tolerance in a subject after allergens are injected regularly over an abbreviated period of weeks or months, also known as "short-course" immunotherapy. Some of the emerging short-course immunotherapy regimens in development aim to minimize the number of injections or administrations to as few as five or three or even one single injection. Such regular exposure can be via sublingual immunotherapy (SLIT), where allergen is daily placed under the tongue of a subject with an allergy. Regular, sustained exposure can also be achieved via weekly, bi-weekly, or monthly subcutaneous injections of allergen extracts (SCIT). Other administration methods of immunotherapy have been also been contemplated, such as oral mucosal immunotherapy (OMIT), whereby the mucosa of the oral cavity is contacted with allergen extracts combined with oral products that are used regularly, such as toothpaste and mouthwash. Despite the differences in administration routes of SLIT, SCIT, and OMIT, all such methods may be referred to generally as "immunotherapy".

In a specific embodiment, provided herein is a method for treating an allergy in a subject, said method comprising (i) diagnosing the subject with an allergy according to the following method: (a) obtaining epithelial cells from a tissue of the subject; (b) contacting the epithelial cells with a composition comprising one or more DARPins capable of causing IgE to dissociate from its receptor (e.g., Fcε-R1); (c) isolating the dissociated IgE; and (d) determining the allergen specificity of the IgE; and (ii) desensitizing (tolerizing) the subject to the allergen/antigen via immunotherapy. In a specific embodiment, said epithelial cells are isolated from the mouth, nose, sublingual space, buccal cavity, esophagus, and/or sinus cavity of the subject. In another specific embodiment, said DARPin comprises one or more of SEQ ID NOs. 1-16. In another specific embodiment, said cells are contacted with a solubilization buffer capable of disrupting cell-cell contacts and/or cell membranes prior to or at the same time they are contacted with said DARPin compositions. The dissociated IgE can be measured using methods known to one of skill in the art, e.g., using a fluorescence-based assay (e.g., ELISA) or by microarray. In a specific embodiment, tolerization of the subject to the allergen/antigen comprises exposing the antigen to the subject once or on a regular basis for at least two weeks to six months and, optimally, continuing for 3-5 years.

As discussed above, the methods for allergy diagnosis provided herein allow for an optimized selection of allergens for a subject's allergy immunotherapy treatment course for a single administration or on a regular basis for at least two weeks to six months, and optimally continuing for 3-5 years. In other embodiments, the methods described herein can be used to monitor a patient's progress during an immunotherapy course. Specifically, a subject who is already determined to have one or more specific allergies can initiate an immunotherapy course for several months and optimally for 3-5 years. During the therapy period, the methods may be used to periodically assess the subject's levels of allergen-specific IgE, which should decrease over time as an additional indication that the therapy is having the intended desensitization effect.

In allergy-related clinical studies, it is common to rely in part on indirect markers of allergic inflammation, such as self-reported symptoms or changes in the use of anti-inflammatory medications. There is a need for additional clinical endpoints and/or assessments of symptomatic tissues that (1) truly reflect the allergic processes, (2) can be standardized, and (3) present minimal invasiveness to clinical study subjects. Accordingly, in a related embodiment, methods may be used as surrogate biomarkers for allergy-relevant inflammation processes, particularly local allergy processes, during clinical studies of subjects with allergies.

The levels of total and specific IgE in a non-allergic, non-diseased subject are normally under tight control by innate homeostatic processes of the immune system. It is known that abnormal levels of IgE in a subject may be indicative of a disease state that is not necessarily an allergic disease. For example, visceral leishmaniasis (VL), caused by infection by the parasite *Leishmania chagasi*, is characterized by depression of the T helper cell type-1 response. This can induce a significantly high titer of *L. chagasi*-specific IgE, which is an important diagnostic tool for identifying cases of VL (Atta et al. 1998, Am. J. Trop. Med. Hyg. 59(3):426-430). Likewise, elevated IgE levels are associated with other parasitic infections including intestinal worms (e.g., helminthes), flukes (e.g., trematodes), and roundworms (e.g., nematodes) (Turner et al, 2005, 7:990-996). Abnormally elevated IgE antibodies have also been suggested to be a factor in cases of infertility (Mathur et al. 1981, 140(8):923-930). Anti-pathogenic IgEs are also known to arise during infections with a multitude of different viruses, including HIV, Parvovirus, variacella zoster virus (VZV), respiratory syncytial virus (RSV), parainfluenza, Epstein-Barr virus, HSV,-1, HSV-2, and Puumala virus (see, e.g., Smith-Norowitz, et al. 2011 Int. J. Med. Sci 8(3):239-244). Accordingly, another aspect provided herein are methods for detecting diseases beyond the scope of allergic diseases, specifically diseases for which an elevated IgE level can support or confirm a diagnosis on the presence and/or severity of the disease. Such an embodiment comprises (i) obtaining disease-relevant or infection-relevant cells from a tissue of the subject; (ii) contacting the cells with a composition comprising one or more DARPins capable of causing IgE to dissociate from its receptor (e.g., Fcε-R1); (iii) isolating the dissociated IgE; and (iv) determining the specificity and levels of the relevant IgE species.

In another aspect, provided herein are novel DARPins that can be used, e.g., to dissociate IgE from its receptor on cells, e.g., epithelial cells, or other allergic disease effector cells to which IgE is bound, of the mouth and/or nose. In a specific embodiment, a novel DARPin sequence provided herein comprises SEQ ID NO:2. In another specific embodiment, a novel DARPin sequence provided herein comprises SEQ ID NO:4. In another specific embodiment, a novel DARPin sequence provided herein comprises SEQ ID NO:6. In another specific embodiment, a novel DARPin sequence provided herein comprises SEQ ID NO:8. In another specific embodiment, a novel DARPin sequence provided herein comprises SEQ ID NO:10. In another specific embodiment, a novel DARPin sequence provided herein comprises SEQ ID NO:12. In another specific embodiment, a novel DARPin sequence provided herein comprises SEQ ID NO:13. In another specific embodiment, a novel DARPin sequence provided herein comprises SEQ ID NO:14. In another specific embodiment, a novel DARPin sequence provided herein comprises SEQ ID NO:15. In another specific embodiment, a novel DARPin sequence provided herein comprises SEQ ID NO:16. In certain embodiments, a DARPin provided herein and/or a DARPin useful in the methods described herein comprises one or more of a signal sequence, a tag (e.g., for use in purification, e.g., a 6× Histidine tag), and/or a cleavage signal (e.g., the amino acid sequence GSENLYFQ (SEQ ID NO:17)). In certain embodiments, a DARPin provided herein and/or a DARPin useful in the methods described herein does not comprise a signal sequence, a tag and/or a cleavage signal.

In another aspect, provided herein are uses of the novel DARPins provided herein.

In one embodiment, DARPins, such as the novel DARPins provided herein (e.g., a DARPin sequence comprising SEQ ID NO:2, SEQ ID NO:4, SEQ ID NO:6, SEQ ID NO:8, SEQ ID NO:10, or SEQ ID NOs.:12-16), are used in a method for determining the allergy profile of a subject, as discussed above and in Section 4.2.

Various therapeutic approaches to allergic diseases have been contemplated that target and modulate the binding of IgE to its high-affinity receptor (FcεRI) on basophils and mast cells. The rationale for such approaches is that decreasing or disrupting the IgE/FcεRI binding in an allergic patient can decrease the availability of cell-bound IgE on mast cells and basophils when inflammation-causing allergen is present, leading to reduced degranulation and resultant inflammatory cascades that lead to allergy symptoms. By example, one such agent, Omalizumab, is a recombinant humanized monoclonal IgG antibody that specifically binds to human free IgE in the blood and interstitial fluid. Omalizumab inhibits the binding of IgE to FcεRI on mast cells and basophils by binding to an epitope on IgE that interferes with FcεRI binding. Omalizumab is currently being used to treat patients with various IgE-triggered allergic inflammations. Similar to Omalizumab, DARPins, such as the novel DARPins provided herein (e.g., a DARPin sequence comprising or consisting of SEQ ID NO:2, SEQ ID NO:4, SEQ ID NO:6, SEQ ID NO:8, SEQ ID NO:10, or SEQ ID NOs.:12-16) are designed to modulate and decrease IgE/FcεRI binding. Accordingly, in another embodiment of the instant invention, DARPins, including the novel DARPins provided herein (e.g., a DARPin sequence comprising or consisting of SEQ ID NO:2, SEQ ID NO:4, SEQ ID NO:6, SEQ ID NO:8, SEQ ID NO:10, or SEQ ID NOs.:12-16), are used in a method of treating, managing, or preventing allergy in a subject, wherein said methods comprise administering a DARPin to the subject in an amount sufficient to cause IgE present on the surface of cells involved in allergic reactions (e.g., mast cells and/or basophils) to dissociate from said cells. In accordance with such methods, when a treated subject is exposed to an allergen, degranulation of the subject's mast cells and/or basophils will not occur, resulting in failure of the subject to mount an allergic response. In specific embodiments, the DARPins are administered systemically or locally to the specific area or tissue where a local allergic inflammation is diagnosed. In related specific embodiments, such therapeutic administration of DARPin may be subcutaneous, intramuscular, intradermal, oral, anal, intravaginal, inhaled, intralymphatic, or through the outer epidermis via a microneedle delivery.

In another aspect, provided herein are kits comprising components sufficient for one of skill in the art to practice the diagnostic methods described herein, e.g., to determine the allergy profile of a subject. See Section 5.

3.1 DEFINITIONS

As used herein, the term "about," when referring to a stated numeric value, indicates a value within plus or minus 10% of the stated numeric value.

As used herein, the terms "subject" and "patient" can be used interchangeably. As used herein, the term "subject" refers to an animal, e.g., a mammal such as a non-primate (e.g., cows, pigs, horses, cats, dogs, rodents, ferrets, etc.) or a primate (e.g., monkey and human). In a specific embodiment, a subject is a human.

As used herein, the terms "treat," "treatment," and "treating" in the context of the administration of a therapy to a subject refer to the reduction or inhibition of the progression and/or duration of an allergic reaction, the reduction or amelioration of the severity of an allergic reaction, and/or the amelioration of one or more symptoms thereof resulting from the administration of one or more therapies.

As used herein, the terms "prevent," "preventing" and "prevention" in the context of the administration of a therapy to a subject refer to the prevention or inhibition of the recurrence, onset, and/or development of an allergic reaction or a symptom thereof in a subject resulting from the administration of a therapy, or a combination of therapies.

As used herein, the terms "manage," "managing," and "management" in the context of the administration of a therapy to a subject refer to the beneficial effects that a subject derives from a therapy or a combination of therapies, while not resulting in a cure of an allergy. In certain embodiments, a subject is administered one or more therapies to "manage" an allergy so as to prevent the progression or worsening of the allergy.

As used herein, the term "antigen" is a term referring to a protein or other biomolecule that is specifically recognized by a particular immunoglobulin or antigen receptor, such as an IgA, IgG, IgE, or IgM. Antigens may be causative agents of IgE-mediated allergic reactions when they are specifically recognized by IgE, in which case they are commonly referred to as "allergens" (see below).

As used herein, the term "allergen" refers to a subtype of "antigen" that is an allergy causing agent. It is the specific antigen that will be recognized by a specific IgE that is produced in a subject with a corresponding IgE-mediated allergy. Thus an allergen is a potential trigger of an allergic inflammation in a subject with an allergy to the specific source of the allergen.

3.2 BRIEF DESCRIPTION OF THE DRAWINGS

FIG. 1 shows the average concentration of IgE obtained from KU-812 cells under various treatment conditions. Each bar represents the average of four experimental replicates. Control untreated samples (light gray bar) contained KU-812 cells with pre-formed IgE/Fcε-R1 complex incubated in PBS alone. DARPin 1 (SEQ ID NO:13) treated samples (D1, dark gray bar) contained KU-812 cells with pre-formed IgE/Fcε-R1 complex treated with 500 ng/mL of DARPin 1. DARPin 2 (SEQ ID NO:14) treated samples (medium gray bar) contained cells with pre-formed IgE/Fcε-R1 complex that were treated with 500 ng/mL of DARPin 2. Both DARPin 1 and DARPin 2 treated samples contained increased levels in IgE levels over the control.

4. DETAILED DESCRIPTION

4.1 DARPins

Designed ankyrin repeat proteins, or DARPins, are approximately 200 amino acid proteins that comprise three domains: an N-terminal capping domain, a C-terminal capping domain, and a variable domain located between the N- and C-terminal domains. Generally, the N- and C-terminal domains are of a defined sequence across DARPins, while the variable domain comprises a combination of defined amino acid residues and DARPin-specific amino acid residues that confer binding specificity on the DARPin. The variable domain sequence with DARPins can be repeated multiple times, and typically DARPins possess two or three variable domains sequence repeats. See, e.g., Binz et al., 2003, J. Mol. Biol. 332:489-503.

Certain DARPins suitable for use in the diagnostic methods described herein, e.g., the DARPins presented in SEQ ID NO:5 and SEQ ID NO:7, are known in the art. See, e.g., Kim et al., 2012, Nature 491:613-617. Further, provided herein are novel DARPins that can be used in accordance with the diagnostic and therapeutic methods described herein. Such DARPins are presented in comprising or consisting of SEQ ID NO:2, SEQ ID NO:4, SEQ ID NO:6, SEQ ID NO:8, SEQ ID NO:10, and SEQ ID NOs.:12-16. One of skill in the art will appreciate that certain modifications to the DARPins described herein can be made without altering the ability of the DARPins to function in the methods described herein, i.e., to dissociate IgE from its receptor. Accordingly, encompassed herein are DARPins that correspond to any one of SEQ ID NOs:1-16 and that are capable of causing IgE to dissociate from its receptor, but that have one, two, three, four, or more amino modifications, substitutions, additions, or deletions relative to the DARPin from which they are based, i.e., SEQ ID NO:1-16.

In certain embodiments, a DARPin provided herein and/or a DARPin useful in the methods described herein comprises one or more of a signal sequence, a tag (e.g., for use in purification, e.g., a 6× Histidine tag), and/or a cleavage signal (e.g., the amino acid sequence GSENLYFQ (SEQ ID NO:17)). In certain embodiments, a DARPin provided herein and/or a DARPin useful in the methods described herein does not comprise a signal sequence, a tag and/or a cleavage signal.

4.2 Methods of Diagnosing Allergy

In a simplified method, the invention encompasses sampling of cells from a patient's area of allergic reaction, particularly cells from the nasal passages, from the oral cavity, or from the GI tract. The cells are then contacted with a preparation of DARPin proteins to release all IgEs from their high-affinity cells receptors. The resulting sample will then contain solubilized, freely accessible IgEs that can be tested for the presence of various specific IgEs, via an immunoassay, that can indicate a specific allergy in the patient. Therefore, in one aspect, provided herein are novel methods for determining the allergy profile of subjects, wherein such methods can be performed using tissue directly involved in allergic reactions, or in tissue samples derived directly from sites of allergic reaction and inflammation.

The methods described herein are non-invasive (epithelial cells of, e.g., the nose and/or mouth, can be obtained by mucosal brush biopsy) and non-harmful (no allergens are introduced to the subject when practicing the methods. The methods provided herein can be used to determine the systemic presence and levels of specific allergy markers, namely IgE with specificity to a known allergen. Accordingly, the test allows for determination of specific allergies giving rise to allergy symptoms in subjects by collecting and processing a sample of cells from a mucosal brush biopsy.

Thus the methods provided herein can, in certain embodiments, be performed on subjects exhibiting symptoms of an allergic reaction (e.g., inflammation), which allows for determination of the specific allergen that is giving rise to the reaction in a subject.

Further, the methods provided herein can be used to determine local presence and levels of specific allergy markers, i.e., IgE with specificity to a known allergen, at the site of allergic symptoms and inflammation (e.g., in the mouth, nose, sinus, esophagus) from a mucosal brush biopsy cell sample. This information, in turn, allows for determination of the specific allergen giving rise to allergy symptoms in subjects at the symptomatic site where the cells were collected with a mucosal brush biopsy (e.g., in the throat, nose, mouth, etc.). Accordingly, the methods provided herein can, in certain embodiments, be performed on subjects exhibiting symptoms of an allergic reaction (e.g., inflammation) at the site of the reaction, thus allowing for determination of the specific allergen giving rise to the local allergy reaction.

In one embodiment, provided herein is a method for diagnosing allergy in a subject, e.g., a human subject, comprising (i) obtaining epithelial cells from a tissue of the subject; (ii) contacting the epithelial cells with a composition comprising one or more DARPins capable of causing IgE to dissociate from its receptor (e.g., Fcε-R1); (iii) isolating the dissociated IgE; and (iv) determining the allergen specificity or specificities of the IgE. In a specific embodiment, said epithelial cells are isolated from the mouth, nose, sublingual space, buccal cavity, esophagus, and/or sinus cavity of the subject. In another specific embodiment, said DARPin comprises or consists of one or more of SEQ ID NOs:1-16, or a sequence with about or at least 85% homology, about or at least 90% homology, about or at least 95% homology, or about or at least 98% homology to any one of SEQ ID NOs. 1-16. In another specific embodiment, said cells are contacted with a solubilization buffer. A solubilization buffer may comprise buffer elements such as HEPES, PBS, TBS, TRIS, Ringer's solution, or IgE-free serum. In certain embodiments, a solubilization buffer may comprise one or more surfactant or detergent agents that can help disrupt cellular membranes such as SDS, Tween 20, Brij 35, Brij 96, Brij 97, Triton X-100, NP-40, or CHAPS. Additionally, in certain embodiments, a solubilization buffer may comprise one or more enzymes that can help disrupt cell-cell contacts such as collagenase, collagenase II, Trypsin, Papain, EDTA, and hyaluronidase. Such a solubilization buffer is designed to support disruption of cell-cell contacts and/or disruption of individual cellular membranes prior to, or simultaneously with, the period in which they are contacted with said DARPin compositions. The dissociated IgE can be measured using methods known to one of skill in the art, e.g., using a fluorescence-based assay (e.g., ELISA), an ImmunoCap (ThermoFisher) or similar IgE detection protocol, or by microarray.

In another embodiment, provided herein is a method for diagnosing allergy in a subject, e.g., a human subject, comprising (i) obtaining epithelial cells from a tissue of the subject; (ii) contacted said cells with a solubilization buffer capable of disrupting the cell membranes; (iii) contacting the resultant composition (i.e., the composition comprising the solubilization buffer/disrupted cells) with a composition comprising one or more DARPins capable of causing IgE to dissociate from its receptor (e.g., Fcε-R1); (iv) isolating the dissociated IgE; and (v) determining the allergen specificity of the IgE. In a specific embodiment, said epithelial cells are isolated from the mouth, nose, sublingual space, buccal cavity, esophagus, and/or sinus cavity of the subject. In another specific embodiment, the isolated epithelial cells are contacted with a solution containing 200 nM-1000 nM of one or more DARPins for 10-40 minutes at room temperature. In another specific embodiment, the one or more DARPins used comprise or consist of one or more of SEQ ID NOs:1-16. The dissociated IgE can be measured using methods known to one of skill in the art, e.g., using a fluorescence-based assay (e.g., ELISA) or by microarray.

In a specific embodiment, a method for diagnosing allergy in a subject provided herein is performed on a subject that has not previously received an allergy test, i.e., the method is performed as a primary diagnostic test. In another specific embodiment, a method for diagnosing allergy in a subject provided herein is performed on a subject that has already received an allergy test, i.e., the method is performed as a secondary diagnostic test to support or additionally clarify a blood or skin test that was inconclusive or inconsistent with the subject's clinical allergy symptoms.

It is known that abnormal levels of lipids (lipemia) in a subject's blood can hinder immunoassays on serum samples for detecting various biomarkers specific IgE in the serum (including ELISAs). Abnormally high levels of lipids from diet, pharmaceutical effects, genetic predisposition, or a combination of these factors, can degrade the accuracy of blood-based biomarker tests that are based on immunoassays (see, e.g., Nikolac, N. Biochem Med (Zagreb). February 2014; 24(1):57-67; and www.questdiagnostics.com/home/physicians/testing-services/specialists/hospitals-lab-staff/specimen-handling/serum-plasma-whole-blood.html). Accordingly, in a further specific embodiment, a method for diagnosing an allergy in a subject is provided herein is performed on a subject who has inaccurate or inconclusive allergy blood test results due to abnormal levels of lipids in the subject's blood.

In certain embodiments, the methods for diagnosing allergy in a subject provided herein can be used to identify an allergy profile of a subject, e.g., to identify most or all of the allergens the subject is allergic to and, conversely, the most or all of the allergens the subject is not allergic to. Comprehensive methods for measuring the allergen-specific profile of IgE are known in the art, e.g., microarray, ImmunoCAP (Thermofisher), and ELISA.

In certain embodiments, the methods for diagnosing allergy in a subject provided herein can be used to determine whether a subject is allergic to a particular allergen of interest. That is, the methods can be used, in combination with an appropriate medical evaluation, to obtain a simple answer of "yes" or "no" with respect to whether or not a subject has a given allergy, e.g., an allergy to peanuts. In other embodiments, the methods provided herein are able to indicate how substantial one or more particular allergies are in a patient, i.e., the methods can stratify patients based on severity of their particular allergies, which is important for determining subsequent disease management and treatment steps. In accordance with such embodiments, assays (e.g., ELISA) can be used to measure whether IgE isolated from the cells of the subject is specific to the allergen of interest.

The methods for diagnosing one or more IgE-mediated allergies in a subject provided herein can be used to identify any type of allergy a subject may be disposed to. In a specific embodiment, the methods for diagnosing allergy in a subject provided herein are used to determine whether or not the subject has a food allergy, e.g., an allergy to peanuts. In another specific embodiment, the methods for diagnosing allergy in a subject provided herein are used to determine whether or not the subject has a seasonal airborne allergy, e.g., an airborne allergy that appears annually during a certain time of each year, such as a tree or grass whose pollen release into the environment peaks on a seasonal cycle. In another specific embodiment, the methods for diagnosing allergy in a subject provided herein are used to determine whether or not the subject has a year-round (perennial) airborne allergy to triggers that the subject is exposed to throughout the year, such as dust mites, cockroaches, cats, and dogs. In a further specific embodiment, the methods for diagnosing allergy in a subject provided herein can be used to determine if a subject has an allergy to a specific stinging insect other venomous or stinging animal.

In further embodiments, the methods for diagnosing one or more IgE-mediated allergies in a subject provided herein can be used to identify any allergy for which there is an available allergen to use as a reagent in the immunoassays which detect and quantitate the sample specific IgEs of the instant invention. Many of such allergens are available and are known in the art. A non-limiting list of allergens that can be used in accordance with the method described herein is presented in Section 4.4, below.

As discussed above, the methods for allergy diagnosis provided herein allow for highly specific identification of local, specific IgEs in subjects, i.e., allergens that are the cause of specific symptoms/reactions identified in the subject. Accordingly, in another aspect, the methods for allergy diagnosis provided herein can be used to identify an insulting allergen, or combination of insulting allergens in a subject, and the subject then can be treated in a manner that results in tolerization of (desensitization to) the insulting allergen/allergens by the subject. For example, tolerance to an allergen/antigen can be achieved in a subject by exposing the subject to the allergen/antigen on a regular basis for a specified time period is sustained for at least two to six months, and, optimally, is sustained for at least 3-5 years. Other immunotherapies are known to generate tolerance in a subject after allergens are injected regularly over an abbreviated period of weeks or months, also known as "short-course" immunotherapy. Some of the emerging short-course immunotherapy regimens in development aim to minimize the number of injections or administrations to as few as five or three or even one single injection. Such regular exposure can be via sublingual immunotherapy (SLIT), where allergen is daily placed under the tongue of a subject with an allergy. Regular, sustained exposure can also be achieved via weekly, bi-weekly, or monthly subcutaneous injections of allergen extracts (SCIT). Other administration methods of immunotherapy have been also been contemplated, such as oral mucosal immunotherapy (OMIT), whereby the mucosa of the oral cavity is contacted with allergen extracts combined with oral products that are used regularly, such as toothpaste and mouthwash. Despite the differences in administration routes of SLIT, SCIT, and OMIT, all such methods may be referred to generally as "immunotherapy".

In a specific embodiment, provided herein is a method for treating an allergy in a subject, said method comprising (i) diagnosing the subject with an allergy according to the following method: (a) obtaining epithelial cells from a tissue of the subject; (b) contacting the epithelial cells with a composition comprising one or more DARPins capable of causing IgE to dissociate from its receptor (e.g., Fcε-R1); (c) isolating the dissociated IgE; and (d) determining the allergen specificity of the IgE; and (ii) desensitizing (tolerizing) the subject to the allergen/antigen via immunotherapy. In a specific embodiment, said epithelial cells are isolated from the mouth, nose, sublingual space, buccal cavity, esophagus, and/or sinus cavity of the subject. In another specific embodiment, said DARPin comprises or consists of one or more of SEQ ID NO:1-16. In another specific embodiment, said cells are contacted with a solubilization buffer capable of disrupting cell-cell contacts and/or cell membranes prior to or at the same time they are contacted with said DARPin compositions. The dissociated IgE can be measured using methods known to one of skill in the art, e.g., using a fluorescence-based assay (e.g., ELISA) or by microarray. In a specific embodiment, tolerization of the subject to the allergen/antigen comprises exposing the antigen to the subject once or on a regular basis for at least two weeks to six months and, optimally, continuing for 3-5 years.

As discussed above, the methods for allergy diagnosis provided herein allow for an optimized selection of allergens for a subject's allergy immunotherapy treatment course for a single administration or on a regular basis for at least two weeks to six months, and optimally continuing for 3-5 years. In other embodiments, the methods described herein can be used to monitor a patient's progress during an immunotherapy course. Specifically, a subject who is already determined to have one or more specific allergies can initiate an immunotherapy course for several months and optimally for 3-5 years. During the therapy period, the methods may be used to periodically assess the subject's levels of allergen-specific IgE, which should decrease over time as an additional indication that the therapy is having the intended desensitization effect.

In allergy-related clinical studies, it is common to rely in part on indirect markers of allergic inflammation, such as self-reported symptoms or changes in the use of anti-inflammatory medications. There is a need for additional clinical endpoints and/or assessments of symptomatic tissues that (1) truly reflect the allergic processes, (2) can be standardized, and (3) present minimal invasiveness to clinical study subjects. Accordingly, in a related embodiment, methods described herein may be used as surrogate biomarkers for allergy-relevant inflammation processes, particularly local allergy processes, during clinical studies of subjects with allergies.

The levels of total and specific IgE in a non-allergic, non-diseased subject are normally under tight control by innate homeostatic processes of the immune system. It is known that abnormal levels of IgE in a subject may be indicative of a disease state that is not necessarily an allergic disease. For example, visceral leishmaniasis (VL), caused by infection by the parasite *Leishmania chagasi*, is characterized by depression of the T helper cell type-1 response. This can induce a significantly high titer of *L. chagasi*-specific IgE, which is an important diagnostic tool for identifying cases of VL (Atta et al. 1998, Am. J. Trop. Med. Hyg. 59(3):426-430). Likewise, elevated IgE levels are associated with other parasitic infections including intestinal worms (e.g., helminthes), flukes (e.g., trematodes), and roundworms (e.g., nematodes) (Turner et al, 2005, 7:990-996). Abnormally elevated IgE antibodies have also been suggested to be a factor in cases of infertility (Mathur et al. 1981, 140(8):923-930). Anti-pathogenic IgEs are also known to arise during infections with a multitude of different viruses, including HIV, Parvovirus, variacella zoster virus (VZV), respiratory syncytial virus (RSV), parainfluenza, Epstein-Barr virus, HSV,-1, HSV-2, and Puumala virus (see, e.g., Smith-Norowitz, et al. 2011 Int. J. Med. Sci 8(3):239-244). Accordingly, another aspect provided herein are methods for detecting diseases beyond the scope of allergic diseases, specifically diseases for which an elevated IgE level can support or confirm a diagnosis on the presence and/or severity of the disease. Such an embodiment comprises (i) obtaining disease-relevant or infection-relevant cells from a tissue of the subject; (ii) contacting the cells with a composition comprising one or more DARPins capable of causing IgE to dissociate from its receptor (e.g., Fcε-R1); (iii) isolating the dissociated IgE; and (iv) determining the specificity and levels of the relevant IgE species.

4.3 Methods of Treating and Preventing Allergy

In one embodiment, DARPins, such as the novel DARPins provided herein (e.g., a DARPin sequence comprising or consisting of SEQ ID NO:2, SEQ ID NO:4, SEQ ID NO:6, SEQ ID NO:8, SEQ ID NO:10, or SEQ ID NOs.:12-16), are used in a method for determining the allergy profile of a subject, as discussed above and in Section 4.2.

Various therapeutic approaches to allergic diseases have been contemplated that target and modulate the binding of IgE to its high-affinity receptor (FcεRI) on basophils and mast cells. The rationale for such approaches is that decreasing or disrupting the IgE/FcεRI binding in an allergic patient can decrease the availability of cell-bound IgE on mast cells and basophils when inflammation-causing allergen is present, leading to reduced degranulation and resultant inflammatory cascades that lead to allergy symptoms. By example, one such agent, Omalizumab, is a recombinant humanized monoclonal IgG antibody that specifically binds to human free IgE in the blood and interstitial fluid. Omalizumab inhibits the binding of IgE to FcεRI on mast cells and basophils by binding to an epitope on IgE that interferes with FcεRI binding. Omalizumab is currently being used to treat patients with various IgE-triggered allergic inflammations. Similar to Omalizumab, DARPins, such as the novel DARPins provided herein (e.g., a DARPin sequence comprising or consisting of SEQ ID NO:2, SEQ ID NO:4, SEQ ID NO:6, SEQ ID NO:8, SEQ ID NO:10, or SEQ ID NOs.:12-16) are designed to modulate and decrease IgE/FcεRI binding. Accordingly, in another embodiment of the instant invention, DARPins, including the novel DARPins provided herein (e.g., a DARPin sequence comprising or consisting of SEQ ID NO:2, SEQ ID NO:4, SEQ ID NO:6, SEQ ID NO:8, SEQ ID NO:10, or SEQ ID NOs.:12-16), are used in a method of treating, managing, or preventing allergy in a subject, wherein said methods comprise administering a DARPin to the subject in an amount sufficient to cause IgE present on the surface of cells involved in allergic reactions (e.g., mast cells and/or basophils) to dissociate from said cells. In accordance with such methods, when a treated subject is exposed to an allergen, degranulation of the subject's mast cells and/or basophils will not occur, resulting in failure of the subject to mount an allergic response. In specific embodiments, the DARPins are administered systemically or locally to the specific area or tissue where a local allergic inflammation is diagnosed. In related specific embodiments, such therapeutic administration of DARPin may be subcutaneous, intramuscular, intradermal, oral, anal, intravaginal, inhaled, intralymphatic, or through the outer epidermis via a microneedle delivery.

4.4 Allergies/Allergens

The methods provided herein can be used to detect whether a subject is allergic to any known allergen. Allergens and allergen extracts that can be used, e.g., in testing of the methods described herein are commercially available. For example, GREER Laboratories Inc. Allergy and Immunotherapy division publishes a brochure entitled "Human Allergy Products and Services" which details a significant list of commonly used allergens (available on-line at www.greerlabs.com/files/catalogs/HumanAllergyCatalog.pdf). GREER also publishes a brochure entitled "Source Materials Products and Services" which details available allergens that can be used as raw materials for production of allergen extracts or more highly purified allergen protein preparations (available online at www.greerlabs.com/files/catalogs/SourceMaterialsCatalog.pdf). Both publications are incorporated herein by reference. Other commercial suppliers of allergens and/or allergen extracts include ALK Abello, Inc., Allermed Labs, Allergy Laboratories, Inc., and HollisterStier. Allergen extracts typically contain multiple proteins, e.g., multiple allergenic proteins, present in the natural form of the allergen. Extracts can be prepared from, e.g., pollens (e.g., of trees, shrubs, grasses, other plants such as those often termed "weeds"), foodstuffs (egg, wheat, soy, shellfish, tree nuts, peanuts, milk, citrus, fish, fruit, etc), animal epithelia, animal skin, animal urine, animal fur, feathers, fungal mycelia or spores, smuts, mites, insects, insect venoms, foods, dusts, etc.

In a specific embodiment, the methods described herein can be used to detect an allergy to grass pollen or grass allergens. Plant pollens are major sources of airborne allergy throughout many areas of the world. Grasses, as used herein, include members of the *Dactylis, Poa, Lolium, Anthoxanthum, Phleum, Festuca, Agrostis,* or *Cynodon* genus, as well as members of the Paoceae family (sometimes termed "true grasses"), rush family (Juncaceae) and sedge family (Cyperaceae). Grasses are distributed widely throughout many regions of the world, with different species having variable importance to allergic populations in different geographical areas. For example, grass species common in at least some regions of Europe and/or the US include *Dactylis glamerata* (orchard grass), *Poa pratensis* (Kentucky bluegrass), *Lolium perenne* (ryegrass), *Anthaxantum adaratum* (sweet vernal), *Phleum pratense* (timothy grass), *Festuca eliatar* (meadow fescue), *Agrostis alba* (redtop), and *Cynodon dactylan* (Bermuda grass).

In another specific embodiment, the methods described herein can be used to detect an allergy to a pollen or an allergen of a tree or shrub. As used herein, trees or shrubs may include acacia, alders (red, hazel, and white), ashes (Arizona, Oregon, red, green, and white), aspen, bayberry, beech, beefwood (Australian pine), box elder, red cedar, salt cedar, cottonwood, elms, *eucalyptus*, hackberry, hazelnut, hickory, locust blossom, mango blossom, red maple, sugar maple, *melaleuca*, mesquite, mulberry, oak, olive, orange, palm, pines, poplar, privet, sweet gum, sycamore, walnut, and willow. Allergens from trees and grasses may also include members of the Cupressaceae family. The Cupressaceae (cypress) family includes a number of species whose common name includes the word "cedar." In some embodiments, the allergy is to pollen or allergen from a species in the subfamily Cupressoideae, e.g., a member of the genus *Chamaecyparis* or *Juniperus* ("juniper"). In other specific embodiments, the allergy that is detected by methods is to pollen or allergens from Cryptameria japonica (family Cupressaceae, subfamily Taxadiaidea), commonly referred to as Sugi or Japanese cedar. In other specific embodiments, the methods described herein may be used to detect an allergy to Ashe juniper (*Juniperus ashei*, family Cupressaceae, sometimes called mountain cedar) and Arizona cypress (*Cupressus arizonica*, family Cupressaceae) pollens or allergens. In other specific embodiments, the methods are used to detect allergies to Italian cypresses (*Cupressus semperverins*, family Cupressaceae), which are known to drive allergic disease symptoms in the Mediterranean region (e.g., France, Italy, Israel). In further specific embodiments, the methods described herein may be used to detect an allergy to the Betulaceae, or birch family, which comprises six genera of deciduous nut-bearing trees and shrubs, including the birches (genus *Betula*), alders (genus *Alnus*), hazels (genus *Corylus*), hornbeams and hop-hornbeams. In another specific embodiment, the methods described herein can be used to detect allergy to the pollen or allergens from a member of the subfamily Betuloideae. In other specific embodiments, the allergy that is detected by methods may be to a pollen or allergen that is from black birch, river birch, spring birch, white birch, or from genus *Betula*, e.g., *Betula verrucosa*.

In another specific embodiment, the methods described herein can be used to detect allergy to a plant. Various plants are significant causes of allergy. Many such plants belong to the families Asteraceae, Amaranthaceae, Urticaceae, Euphorbiaceae, and Plantaginaceae. Accordingly, in another specific embodiment, the methods described herein can be used to detect an allergy to a pollen or allergen from a plant or weed of the Asteraceae, Amaranthaceae, Urticaceae, Euphorbiaceae, or Plantaginaceae family. Specific examples of weed plants whose allergies may be detected by methods include allscale, *baccharis*, burrobush, careless weed, cocklebur, dock, dog fennel, feverfew, firebush, goldenrod, goosefoot, hemp, iodine bush, lamb's quarter, lenscale, march elder, mugwort, nettle, Palmer's amaranth, pellitory, pigweed, plaintain, rabbit bush, ragweed, Russian thistle, sagebrush, saltbush, sorrel, and wingscale. Ragweeds (*Ambrosia* species), for example, are a genus of flowering plants from the sunflower family (Asteraceae) and represent a highly significant cause of allergy in North America that is becoming increasingly important in Europe.

Dust mites are significant sources of allergy in many areas of the world. In another specific embodiment, the methods described herein can be used to detect an allergy to allergens from dust mites, including from feces, excretions, and particles of the mite body. As used herein, dust mite species of importance include, for example, *Dermatophagoides farinae*, *Dermatophagoides pteronyssinus*, *Tyrophagus putrescentiae*, and *Blomia tropicalis*.

In another specific embodiments, the methods described herein may be used to detect an allergy to allergens originating from animals. As used herein, animal allergens include proteins from dander, feathers, hair, skin, fur, saliva, and excretions (e.g., urine) that are generated by an animal. Domesticated animals such as cats (*Felis domesticus*) and dogs (*Canis lupus familiaris*) are common sources of allergy-triggering animal allergens. The methods described herein can be used for detecting allergies to animal allergens generated from cats, dogs, cattle, gerbil, goat, guinea pig, hamster, hog, horse, mouse, rabbit, rat, canary, chicken, duck, goose, parakeet, or human.

Insects and insect venoms are notable sources of allergens that can trigger allergies. Accordingly, in another specific embodiment, the methods described herein can be used to detect allergies to allergens from insects, insect venoms, insect bodies, insect excretions, and insect feces. As used herein, insects may include cockroach species, for example, *Blattella germanica* (German cockroach) and *Periplaneta Americana* (American cockroach), and *Blatta orientalis* (Oriental cockroach). As used herein, insects also include black ant, fire ant, carpenter ant, caddisfly, deer fly, house fly, mayfly, mosquito, and moth. As used herein, insect venom includes venom from insects of the order Hymenoptera, e.g., bees, hornets, or wasps that are potential causes of severe allergic reactions. Other insect venoms of interest include those from European hornet (*Vespa crabro*), honey bee (*Apis mellifera*), hornet (*Dolichovespula* spp.), paper wasp (*Polistes* spp.), yellow jacket (*Vespula* spp.), white (bald)-faced hornet (*Dolichovespula maculata*), and yellow hornet (*Dolichovespula arenaria*).

Fungi are significant sources of allergy. Accordingly, in another specific embodiment, the methods described herein can be used to detect allergies to fungi. As used herein, fungi includes *Alternaria* (e.g., *Alternaria alternata* (*Alternaria* rot fungus)), *Cladosporium* (e.g., *Cladosporium herbarum*, *Cladosporium cladosporioides*), *Aspergillus* (e.g., *Aspergillus fumigatus*, *Aspergillus niger*), *Fusarium*, and *Penicillium*.

In another specific embodiment, the methods described herein can be used to detect allergies to plant-derived foods, or more specifically, allergies that manifest upon oral consumption of specific foodstuffs. As used herein, plant-derived foods may include apple, apricot, banana, barley, lima bean, navy bean, sting bean, blueberry, broccoli, buckwheat, cabbage, cantaloupe, carrot, cauliflower, celery, cherry, chocolate, cinnamon, coffee, corn, cranberry, cucumber, garlic, ginger, grape, grapefruit, hops, lemon, lettuce, malt, mushroom, mustard, nutmeg, oat, olive, onion, orange, pea, peach, pear, pepper (green and black), pineapple, sweet potato, white potato, raspberry, rice, rye, sesame seed, soybean, spinach, squash, strawberry, tomato, vanilla bean, watermelon, and wheat.

In another specific embodiment, the methods described herein can be used to detect allergies to animal-derived foods. As used herein, animal-derived foods include beef, lamb, pork, chicken meat, turkey, egg white, egg yolk, whole egg, and milk.

In another specific embodiment, the methods described herein can be used to detect allergies to fish and shellfish food. As used herein, fish and shellfish foods may include bass, catfish, clam, codfish, crab, flounder, lobster, mackerel, oyster, perch, salmon, scallop, shrimp, trout, and tuna.

In another specific embodiment, the methods described herein can be used to detect allergies to nuts. As used herein, nuts may include almond, brazil nut, cashew, coconut, hazelnut, peanut, pecan, English walnut, and black walnut.

5. KITS

Provided herein are kits comprising components sufficient for one of skill in the art to practice the diagnostic methods described herein, e.g., to determine the allergy profile of a subject.

In a specific embodiment, provided herein is a kit comprising (i) a container comprising a composition that comprises DARPins capable of causing IgE to dissociate from its receptor and (ii) an apparatus for collecting cells from a tissue of a subject, e.g., a brush for use in a mucosal brush biopsy. An exemplary use of such a kit to determine the allergy profile of a subject is as follows: epithelial cells from the mouth of a subject are obtained using the provided apparatus (e.g., by mucosal brush biopsy) and placed in the container comprising the DARPins, resulting in dissociation of IgE from its receptor on the collected cells. The IgE can then be isolated and allergen specificity of the IgE can be assessed using methods known in the art, e.g., using a fluorescence-based assay (e.g., ELISA) or by microarray.

One of skill in the art will appreciate that the kits provided herein can be prepared in certain ways while still allowing for their use in practicing one or more of the methods provided herein. For example, in certain embodiments, the kits provided herein, in addition to comprising an apparatus for collecting cells from a tissue of a subject (e.g., a brush for use in a mucosal brush biopsy) and a composition that comprises DARPins capable of causing IgE to dissociate from its receptor, can comprise a solubilization buffer capable of disrupting cell-cell contacts and/or cell membranes of IgE receptor-expressing cells, but that does not alter antigen specificity of the IgE for its cognate antigen. In accordance with such embodiments, the composition that comprises DARPins capable of causing IgE to dissociate from its receptor can be added to the container comprising a solubilization buffer after the collected cells have been added to the container comprising a solubilization buffer. An exemplary use of such a kit to determine the allergy profile of a subject is as follows: epithelial cells from the mouth of a subject are obtained using the provided apparatus (e.g., by mucosal brush biopsy) and placed in the container comprising the solubilization buffer, resulting in disruption of the cell membranes of the collected IgE receptor expressing cells; the composition that comprises DARPins is added to the container comprising solubilization buffer, resulting in dissociation of IgE from its receptor on the collected cells. The IgE can then be isolated and allergen specificity of the IgE can be assessed using methods known in the art, e.g., using a fluorescence-based assay (e.g., ELISA) or by microarray.

In certain embodiments, the kits provided herein comprise disposables, e.g., sterile wipes, disposable paper goods, gloves, or the like, which can facilitate preparation of a subject for analysis in accordance with the methods described herein.

In certain embodiments, the kits provided herein comprise a label or labeling (and/or a package insert) with instructions for using the components provided in the kits.

TABLE 1

List of Sequences

| SEQ ID NO | Sequence | Description |
|---|---|---|
| 1 | MKHHHHHHGSDLGKKLLEAARAGQDDEV RILTANGADVNANDYWGHTPLHLAAMLGHL EIVEVLLKNGADVNATGNTG RTPLHLAAWA DHLEIVEVLLKHGADVNAQD KFGKTAFDIS IDNGNEDLAEILQKL | DARPin precursor sequence that comprises a leader sequence (bold) followed by six histidine residues (HIS-tag) followed by a DARPin sequence (underlined) |
| 2 | MKRHHHHHHGSDLGKKLLEAARAGQDDEV RILTANGADVNANDYWGHTPLHLAAMLGHL EIVDVLLANGADVNASGNTG RTPLHLAAWA DHLEIVDVLLAHGADVNASD KFGKTAFDIS IDNGNEDLAEILQKL | DARPin precursor sequence that comprises a leader sequence (bold) followed by six histidine residues (HIS-tag) followed by a DARPin sequence |
| 3 | MKHHHHHHGSDLGKKLLEAARAGQDDEV RILTANGADVNATGNTGRTPLHLAAWADHL EIVEVLLKHGADVNATGNTG RTPLHLAAWA DHLEIVEVLLKHGADVNAQD KFGKTAFDIS IDNGNEDLAEILQKL | DARPin precursor sequence that comprises a leader sequence (bold) followed by six histidine residues (HIS-tag) followed by a DARPin sequence |
| 4 | MKHHHHHHGSDLGKKLLEAARAGQDDEV RILTANGADVNATGNTGRTP LHLAAWADHL EIVDVLLAHGADVNASGNTGRTPLHLAAWA DHLEIVDVLLAHGADVNASDKFGKTAFDIS IDNGNEDLAEILQKL | DARPin precursor sequence that comprises a leader sequence (bold) followed by six histidine residues (HIS-tag) followed by a DARPin sequence |
| 5 | MRGSHHHHHHGSDLGKKLLEAARAGQDDEV RILTANGADVNANDYWGHTPLHLAAMLGHL EIVEVLLKNGADVNATGNTG RTPLHLAAWA DHLEIVEVLLKHGADVNAQD KFGKTAFDIS IDNGNEDLAEILQKL | DARPin precursor sequence that comprises a leader sequence (bold) followed by six histidine residues (HIS-tag) followed by a DARPin sequence |
| 6 | MRGSHHHHHHGSDLGKKLLEAARAGQDDEV RILTANGADVNANDYWGHTPLHLAAMLGHL EIVDVLLANGADVNASGNTG RTPLHLAAWA DHLEIVDVLLAHGADVNASD KFGKTAFDIS IDNGNEDLAEILQKL | DARPin precursor sequence that comprises a leader sequence (bold) followed by six histidine residues (HIS-tag) followed by a DARPin sequence |
| 7 | MRGSHHHHHHGSDLGKKLLEAARAGQDDEV RILTANGADVNATGNTGRTPLHLAAWADHL EIVEVLLKHGADVNATGNTG RTPLHLAAWA DHLEIVEVLLKHGADVNAQD KFGKTAFDIS IDNGNEDLAEILQKL | DARPin precursor sequence that comprises a leader sequence (bold) followed by six histidine residues (HIS- |

TABLE 1-continued List of Sequences

| SEQ ID NO | Sequence | Description |
|---|---|---|
| | | tag) followed by a DARPin sequence |
| 8 | MRGSHHHHHHGSDLGKKLLEAARAGQDDEV RILTANGADVNATGNTGRTP LHLAAWADHL EIVDVLLAHGADVNASGNTGRTPLHLAAWA DHLEIVDVLLAHGADVNASDKFGKTAFDIS IDNGNEDLAEILQKL | DARPin precursor sequence that comprises a leader sequence (bold) followed by six histidine residues (HIS-tag) followed by a DARPin sequence |
| 9 | GSDLGKKLLEAARAGQDDEV RILTANGADVNANDYWGHTPLHLAAMLGHL EIVEVLLKNGADVNATGNTG RTPLHLAAWA DHLEIVEVLLKHGADVNAQD KFGKTAFDIS IDNGNEDLAEILQKL | DARPin sequence presented in SEQ ID NOs: 1 and 5 |
| 10 | GSDLGKKLLEAARAGQDDEV RILTANGADVNANDYWGHTPLHLAAMLGHL EIVDVLLANGADVNASGNTG RTPLHLAAWA DHLEIVDVLLAHGADVNASD KFGKTAFDIS IDNGNEDLAEILQKL | DARPin sequence presented in SEQ ID NOs: 2 and 6 |
| 11 | GSDLGKKLLEAARAGQDDEV RILTANGADVNATGNTGRTPLHLAAWADHL EIVEVLLKHGADVNATGNTG RTPLHLAAWA DHLEIVEVLLKHGADVNAQD KFGKTAFDIS IDNGNEDLAEILQKL | DARPin sequence presented in SEQ ID NOs: 3 and 7 |
| 12 | GSDLGKKLLEAARAGQDDEV RILTANGADVNATGNTGRTP LHLAAWADHL EIVDVLLAHGADVNASGNTGRTPLHLAAWA DHLEIVDVLLAHGADVNASDKFGKTAFDIS IDNGNEDLAEILQKL | DARPin sequence presented in SEQ ID NOs: 4 and 8 |
| 13 | MKHHHHHH*GSENLYFQ*GSDLGKKLLEAA RAGQDDEV RILTANGADVNANDYWGHTPLHLAAMLGHL EIVEVLLKNGADVNATGNTG RTPLHLAAWA DHLEIVEVLLKHGADVNAQD KFGKTAFDIS IDNGNEDLAEILQKL | DARPin precursor sequence that comprises a leader sequence (bold) followed by six histidine residues (HIS-tag) followed by a cleavage sequence (italics) followed by a DARPin sequence (underlined) |
| 14 | MKHHHHHH*GSENLYFQ*GSDLGKKLLEAA RAGQDDEV RILTANGADVNANDYWGHTPLHLAAMLGHL EIVDVLLANGADVNASGNTG RTPLHLAAWA DHLEIVDVLLAHGADVNASD KFGKTAFDIS IDNGNEDLAEILQKL | DARPin precursor sequence that comprises a leader sequence (bold) followed by six histidine residues (HIS-tag) followed by a cleavage sequence (italics) followed by a DARPin sequence (underlined) |
| 15 | MKHHHHHH*GSENLYFQ*GSDLGKKLLEAA RAGQDDEV RILTANGADVNATGNTGRTPLHLAAWADHL EIVEVLLKHGADVNATGNTG RTPLHLAAWA DHLEIVEVLLKHGADVNAQD KFGKTAFDIS IDNGNEDLAEILQKL | DARPin precursor sequence that comprises a leader sequence (bold) followed by six histidine residues (HIS-tag) followed by a cleavage sequence (italics) followed by a DARPin sequence (underlined) |
| 16 | MKHHHHHH*GSENLYFQ*GSDLGKKLLE AARAGQDDEV RILTANGADVNATGNTGRTP LHLAAWADHL EIVDVLLAHGADVNASGNTGRTPLHLAAWA DHLEIVDVLLAHGADVNASDKFGKTAFDIS IDNGNEDLAEILQKL | DARPin precursor sequence that comprises a leader sequence (bold) followed by six histidine residues (HIS-tag) followed by a cleavage sequence |

TABLE 1-continued

List of Sequences

| SEQ ID NO | Sequence | Description |
|---|---|---|
| | | (italics) followed by a DARPin sequence (underlined) |
| 17 | GSENLYFQ | Cleavage Site |

6. EXAMPLES 6.1 IgE Dissociation from Human Cells Using DARPins

DARPin 1 (SEQ ID NO: 13) and DARPin 2 (SEQ ID NO: 14), used in this Example, were generated from SEQ ID NOs: 1 and 2, respectively. A cleavage site, GSENLYFQ (SEQ ID NO: 17), was inserted after the 6x-HIS-tag present in each sequence (SEQ ID NO: 1 and SEQ ID NO. 2) to facilitate removal of the leader sequence and HIS-tag, if desired. Nucleic acids encoding SEQ ID NO: 13 and SEQ ID NO. 14 were cloned into the pET26b vector and transformed into E. coli. The resultant proteins, produced in E. coli, were purified using HisTrap FF columns (GE Healthcare) and eluted using Imidazole. The purified DARPins were then used to test their ability to dissociate IgE in cell culture.

Human basophilic cells (ATCC) expressing the IgE-specific Fcε-R1 receptor were grown in culture until they reached optimal confluence. The cells were harvested by spinning at 200×g for 7 minutes, then the media was aspirated and the cells washed twice with PBS. The cells were re-suspended in PBS containing human IgE antibody (Millipore) at a concentration of 1 µg/µl and incubated for 20 minutes at room temperature to allow formation of IgE/Fcε-R1 complexes. Next, the cells were pelleted by spinning at 200×g for 5 minutes, the supernatant aspirated, the cells washed twice in PBS and then re-suspended with either PBS alone (untreated) or PBS pre-diluted with DARPin 1 (SEQ ID NO: 13) and DARPin 2 (SEQ ID NO: 14) at a concentration of 500 µg/ml. The cells were then incubated for 20 minutes at room temperature with gentle mixing. The cells were then spun at 125×g and the supernatant was removed. The supernatant was then used to perform ELISA analysis (Affymetrix) to determine the level of IgE. ELISA plates were coated with purified anti-human IgE antibody, the IgE labeled with HRP-conjugated anti-IgE, and detected with TMB substrate solution. The ELISA plates were in a 96-well format and were read on a BioTek µQuant Microplate Spectrophotometer.

As demonstrated in FIG. 1, both DARPin 1 and DARPin 2 dissociated IgE from its high affinity receptor. In contrast, minimal amounts of IgE were detected from untreated samples.

All publications cited in this specification are herein incorporated by reference as if each individual publication or patent application were specifically and individually indicated to be incorporated by reference. Although the foregoing has been described in some detail by way of illustration and example for purposes of clarity of understanding, it will be readily apparent to those of ordinary skill in the art in light of the teachings provided herein that certain changes and modifications may be made thereto without departing from the spirit or scope of the appended claims.

What is claimed:

1. A method for diagnosing allergy in a subject comprising (i) obtaining a population of cells from a tissue of the subject, wherein said population of cells comprises cells that comprise an IgE receptor with bound IgE; (ii) contacting said cells with a composition comprising one or more DARPins capable of causing IgE to dissociate from an IgE receptor; (iii) determining the allergen specificity of the isolated IgE, wherein said one or more DARPins comprises one or more of SEQ ID NOs: 1-16.

2. The method of claim 1, wherein said population of cells is obtained from the mouth, nose, sublingual space, buccal cavity, esophagus, sinus cavity, stomach, and/or blood of the subject.

3. The method of claim 1, wherein said cells are epithelial cells.

4. The method of claim 1, wherein the allergen specificity of the IgE is measured using a fluorescence-based assay or a colorimetric assay.

5. The method of claim 4, wherein said fluorescence-based or colorimetric assay is an ELISA.

6. The method of claim 1, wherein the allergen specificity of the IgE is measured using microarray.

7. The method of claim 1, wherein the allergen specificity of the IgE is measured using a qualitative or quantitative assay.

8. The method of claim 1, wherein said method further comprises contacting said population of cells with a solubilization buffer capable of disrupting cell membranes prior to or at the same time that said cells are contacted with said DARPin composition.

9. The method of claim 1, wherein said method is used to determine an allergy profile in said subject.

10. The method of claim 1, wherein said method is used to determine whether said subject is allergic to a specific allergen.

11. The method of claim 10, wherein said specific allergen is an allergen from:
(i) a plant-derived food;
(ii) an animal-derived food;
(iii) fish or shellfish;
(iv) a nut; or
(v) a plant pollen, an animal, a dust mite, an insect, or a fungus.

12. The method of claim 9, further comprising subjecting the subject to immunotherapy to desensitize the subject to said specific allergen.

13. A DARPin comprising an amino acid sequence comprising any one of SEQ ID NOs. 1-4, 6, 8, 10 and 12-16.

14. The DARPin of claim 13 comprising an amino acid sequence comprising any one of SEQ ID NOs. 2, 4, 6, or 8.

15. The DARPin of claim 13 comprising an amino acid sequence comprising any one of SEQ ID NOs. 10 and 12.

16. The DARPin of claim 13 comprising an amino acid sequence comprising SEQ ID NOs. 13-16.

17. The DARPin of claim 13 further comprising a pharmaceutically accepted carrier.

18. A kit for use in diagnosing allergy, said kit comprising (i) a container comprising a composition that comprises one or more DARPins capable of causing IgE to dissociate from its receptor, wherein said one or more DARPins comprises one or more of SEQ ID NOs: 1-16; and (ii) an apparatus for collecting cells from a tissue of a subject.

19. The method of claim 10, further comprising subjecting the subject to immunotherapy to desensitize the subject to said specific allergen.

* * * * *

SEQUENCE LISTING

```
<160> NUMBER OF SEQ ID NOS: 17

<210> SEQ ID NO 1
<211> LENGTH: 133
<212> TYPE: PRT
<213> ORGANISM: Artificial Sequence
<220> FEATURE:
<223> OTHER INFORMATION: Synthetic peptide (DARPin sequence)

<400> SEQUENCE: 1

Met Lys His His His His His His Gly Ser Asp Leu Gly Lys Lys Leu
1               5                   10                  15

Leu Glu Ala Ala Arg Ala Gly Gln Asp Asp Glu Val Arg Ile Leu Thr
                20                  25                  30

Ala Asn Gly Ala Asp Val Asn Ala Asn Asp Tyr Trp Gly His Thr Pro
            35                  40                  45

Leu His Leu Ala Ala Met Leu Gly His Leu Glu Ile Val Glu Val Leu
        50                  55                  60

Leu Lys Asn Gly Ala Asp Val Asn Ala Thr Gly Asn Thr Gly Arg Thr
65                  70                  75                  80

Pro Leu His Leu Ala Ala Trp Ala Asp His Leu Glu Ile Val Glu Val
                85                  90                  95
```

Leu Leu Lys His Gly Ala Asp Val Asn Ala Gln Asp Lys Phe Gly Lys
            100                 105                 110

Thr Ala Phe Asp Ile Ser Ile Asp Asn Gly Asn Glu Asp Leu Ala Glu
        115                 120                 125

Ile Leu Gln Lys Leu
        130

<210> SEQ ID NO 2
<211> LENGTH: 133
<212> TYPE: PRT
<213> ORGANISM: Artificial Sequence
<220> FEATURE:
<223> OTHER INFORMATION: Synthetic peptide (DARPin sequence)

<400> SEQUENCE: 2

Met Lys His His His His His His Gly Ser Asp Leu Gly Lys Lys Leu
1               5                   10                  15

Leu Glu Ala Ala Arg Ala Gly Gln Asp Asp Glu Val Arg Ile Leu Thr
            20                  25                  30

Ala Asn Gly Ala Asp Val Asn Ala Asn Asp Tyr Trp Gly His Thr Pro
        35                  40                  45

Leu His Leu Ala Ala Met Leu Gly His Leu Glu Ile Val Asp Val Leu
    50                  55                  60

Leu Ala Asn Gly Ala Asp Val Asn Ala Ser Gly Asn Thr Gly Arg Thr
65                  70                  75                  80

Pro Leu His Leu Ala Ala Trp Ala Asp His Leu Glu Ile Val Asp Val
                85                  90                  95

Leu Leu Ala His Gly Ala Asp Val Asn Ala Ser Asp Lys Phe Gly Lys
            100                 105                 110

Thr Ala Phe Asp Ile Ser Ile Asp Asn Gly Asn Glu Asp Leu Ala Glu
        115                 120                 125

Ile Leu Gln Lys Leu
        130

<210> SEQ ID NO 3
<211> LENGTH: 133
<212> TYPE: PRT
<213> ORGANISM: Artificial Sequence
<220> FEATURE:
<223> OTHER INFORMATION: Synthetic peptide (DARPin sequence)

<400> SEQUENCE: 3

Met Lys His His His His His His Gly Ser Asp Leu Gly Lys Lys Leu
1               5                   10                  15

Leu Glu Ala Ala Arg Ala Gly Gln Asp Asp Glu Val Arg Ile Leu Thr
            20                  25                  30

Ala Asn Gly Ala Asp Val Asn Ala Thr Gly Asn Thr Gly Arg Thr Pro
        35                  40                  45

Leu His Leu Ala Ala Trp Ala Asp His Leu Glu Ile Val Glu Val Leu
    50                  55                  60

Leu Lys His Gly Ala Asp Val Asn Ala Thr Gly Asn Thr Gly Arg Thr
65                  70                  75                  80

Pro Leu His Leu Ala Ala Trp Ala Asp His Leu Glu Ile Val Glu Val
                85                  90                  95

Leu Leu Lys His Gly Ala Asp Val Asn Ala Gln Asp Lys Phe Gly Lys
            100                 105                 110

Thr Ala Phe Asp Ile Ser Ile Asp Asn Gly Asn Glu Asp Leu Ala Glu

Ile Leu Gln Lys Leu
    130

<210> SEQ ID NO 4
<211> LENGTH: 133
<212> TYPE: PRT
<213> ORGANISM: Artificial Sequence
<220> FEATURE:
<223> OTHER INFORMATION: Synthetic peptide (DARPin sequence)

<400> SEQUENCE: 4

Met Lys His His His His His Gly Ser Asp Leu Gly Lys Lys Leu
1               5                   10                  15

Leu Glu Ala Ala Arg Ala Gly Gln Asp Asp Glu Val Arg Ile Leu Thr
            20                  25                  30

Ala Asn Gly Ala Asp Val Asn Ala Thr Gly Asn Thr Gly Arg Thr Pro
        35                  40                  45

Leu His Leu Ala Ala Trp Ala Asp His Leu Glu Ile Val Asp Val Leu
    50                  55                  60

Leu Ala His Gly Ala Asp Val Asn Ala Ser Gly Asn Thr Gly Arg Thr
65                  70                  75                  80

Pro Leu His Leu Ala Ala Trp Ala Asp His Leu Glu Ile Val Asp Val
                85                  90                  95

Leu Leu Ala His Gly Ala Asp Val Asn Ala Ser Asp Lys Phe Gly Lys
            100                 105                 110

Thr Ala Phe Asp Ile Ser Ile Asp Asn Gly Asn Glu Asp Leu Ala Glu
        115                 120                 125

Ile Leu Gln Lys Leu
    130

<210> SEQ ID NO 5
<211> LENGTH: 135
<212> TYPE: PRT
<213> ORGANISM: Artificial Sequence
<220> FEATURE:
<223> OTHER INFORMATION: Synthetic peptide (DARPin sequence)

<400> SEQUENCE: 5

Met Arg Gly Ser His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Thr Ala Asn Gly Ala Asp Val Asn Ala Asn Asp Tyr Trp Gly His
        35                  40                  45

Thr Pro Leu His Leu Ala Ala Met Leu Gly His Leu Glu Ile Val Glu
    50                  55                  60

Val Leu Leu Lys Asn Gly Ala Asp Val Asn Ala Thr Gly Asn Thr Gly
65                  70                  75                  80

Arg Thr Pro Leu His Leu Ala Ala Trp Ala Asp His Leu Glu Ile Val
                85                  90                  95

Glu Val Leu Leu Lys His Gly Ala Asp Val Asn Ala Gln Asp Lys Phe
            100                 105                 110

Gly Lys Thr Ala Phe Asp Ile Ser Ile Asp Asn Gly Asn Glu Asp Leu
        115                 120                 125

Ala Glu Ile Leu Gln Lys Leu
    130                 135

<210> SEQ ID NO 6
<211> LENGTH: 135
<212> TYPE: PRT
<213> ORGANISM: Artificial Sequence
<220> FEATURE:
<223> OTHER INFORMATION: Synthetic peptide (DARPin sequence)

<400> SEQUENCE: 6

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Thr Ala Asn Gly Ala Asp Val Asn Ala Asn Asp Tyr Trp Gly His
        35                  40                  45

Thr Pro Leu His Leu Ala Ala Met Leu Gly His Leu Glu Ile Val Asp
    50                  55                  60

Val Leu Leu Ala Asn Gly Ala Asp Val Asn Ala Ser Gly Asn Thr Gly
65                  70                  75                  80

Arg Thr Pro Leu His Leu Ala Ala Trp Ala Asp His Leu Glu Ile Val
                85                  90                  95

Asp Val Leu Leu Ala His Gly Ala Asp Val Asn Ala Ser Asp Lys Phe
            100                 105                 110

Gly Lys Thr Ala Phe Asp Ile Ser Ile Asp Asn Gly Asn Glu Asp Leu
        115                 120                 125

Ala Glu Ile Leu Gln Lys Leu
    130                 135

<210> SEQ ID NO 7
<211> LENGTH: 135
<212> TYPE: PRT
<213> ORGANISM: Artificial Sequence
<220> FEATURE:
<223> OTHER INFORMATION: Synthetic peptide (DARPin sequence)

<400> SEQUENCE: 7

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
            20                  25                  30

Leu Thr Ala Asn Gly Ala Asp Val Asn Ala Thr Gly Asn Thr Gly Arg
        35                  40                  45

Thr Pro Leu His Leu Ala Ala Trp Ala Asp His Leu Glu Ile Val Glu
    50                  55                  60

Val Leu Leu Lys His Gly Ala Asp Val Asn Ala Thr Gly Asn Thr Gly
65                  70                  75                  80

Arg Thr Pro Leu His Leu Ala Ala Trp Ala Asp His Leu Glu Ile Val
                85                  90                  95

Glu Val Leu Leu Lys His Gly Ala Asp Val Asn Ala Gln Asp Lys Phe
            100                 105                 110

Gly Lys Thr Ala Phe Asp Ile Ser Ile Asp Asn Gly Asn Glu Asp Leu
        115                 120                 125

Ala Glu Ile Leu Gln Lys Leu
    130                 135

<210> SEQ ID NO 8
<211> LENGTH: 135
<212> TYPE: PRT
<213> ORGANISM: Artificial Sequence

```
<220> FEATURE:
<223> OTHER INFORMATION: Synthetic peptide (DARPin sequence)

<400> SEQUENCE: 8

Met Arg Gly Ser His His His His His His Gly Ser Asp Leu Gly Lys
1               5                   10                  15

Lys Leu Leu Glu Ala Ala Arg Ala Gly Gln Asp Asp Glu Val Arg Ile
                20                  25                  30

Leu Thr Ala Asn Gly Ala Asp Val Asn Ala Thr Gly Asn Thr Gly Arg
            35                  40                  45

Thr Pro Leu His Leu Ala Ala Trp Ala Asp His Leu Glu Ile Val Asp
        50                  55                  60

Val Leu Leu Ala His Gly Ala Asp Val Asn Ala Ser Gly Asn Thr Gly
65                  70                  75                  80

Arg Thr Pro Leu His Leu Ala Ala Trp Ala Asp His Leu Glu Ile Val
                85                  90                  95

Asp Val Leu Leu Ala His Gly Ala Asp Val Asn Ala Ser Asp Lys Phe
                100                 105                 110

Gly Lys Thr Ala Phe Asp Ile Ser Ile Asp Asn Gly Asn Glu Asp Leu
            115                 120                 125

Ala Glu Ile Leu Gln Lys Leu
        130                 135

<210> SEQ ID NO 9
<211> LENGTH: 125
<212> TYPE: PRT
<213> ORGANISM: Artificial Sequence
<220> FEATURE:
<223> OTHER INFORMATION: Synthetic peptide (DARPin sequence)

<400> SEQUENCE: 9

Gly Ser Asp Leu Gly Lys Lys Leu Leu Glu Ala Ala Arg Ala Gly Gln
1               5                   10                  15

Asp Asp Glu Val Arg Ile Leu Thr Ala Asn Gly Ala Asp Val Asn Ala
                20                  25                  30

Asn Asp Tyr Trp Gly His Thr Pro Leu His Leu Ala Ala Met Leu Gly
            35                  40                  45

His Leu Glu Ile Val Glu Val Leu Leu Lys Asn Gly Ala Asp Val Asn
        50                  55                  60

Ala Thr Gly Asn Thr Gly Arg Thr Pro Leu His Leu Ala Ala Trp Ala
65                  70                  75                  80

Asp His Leu Glu Ile Val Glu Val Leu Leu Lys His Gly Ala Asp Val
                85                  90                  95

Asn Ala Gln Asp Lys Phe Gly Lys Thr Ala Phe Asp Ile Ser Ile Asp
                100                 105                 110

Asn Gly Asn Glu Asp Leu Ala Glu Ile Leu Gln Lys Leu
            115                 120                 125

<210> SEQ ID NO 10
<211> LENGTH: 125
<212> TYPE: PRT
<213> ORGANISM: Artificial Sequence
<220> FEATURE:
<223> OTHER INFORMATION: Synthetic peptide (DARPin sequence)

<400> SEQUENCE: 10

Gly Ser Asp Leu Gly Lys Lys Leu Leu Glu Ala Ala Arg Ala Gly Gln
1               5                   10                  15
```

```
Asp Asp Glu Val Arg Ile Leu Thr Ala Asn Gly Ala Asp Val Asn Ala
            20                  25                  30

Asn Asp Tyr Trp Gly His Thr Pro Leu His Leu Ala Ala Met Leu Gly
        35                  40                  45

His Leu Glu Ile Val Asp Val Leu Leu Ala Asn Gly Ala Asp Val Asn
    50                  55                  60

Ala Ser Gly Asn Thr Gly Arg Thr Pro Leu His Leu Ala Ala Trp Ala
65                  70                  75                  80

Asp His Leu Glu Ile Val Asp Val Leu Leu Ala His Gly Ala Asp Val
                85                  90                  95

Asn Ala Ser Asp Lys Phe Gly Lys Thr Ala Phe Asp Ile Ser Ile Asp
            100                 105                 110

Asn Gly Asn Glu Asp Leu Ala Glu Ile Leu Gln Lys Leu
        115                 120                 125

<210> SEQ ID NO 11
<211> LENGTH: 125
<212> TYPE: PRT
<213> ORGANISM: Artificial Sequence
<220> FEATURE:
<223> OTHER INFORMATION: Synthetic peptide (DARPin sequence)

<400> SEQUENCE: 11

Gly Ser Asp Leu Gly Lys Lys Leu Leu Glu Ala Ala Arg Ala Gly Gln
1               5                   10                  15

Asp Asp Glu Val Arg Ile Leu Thr Ala Asn Gly Ala Asp Val Asn Ala
            20                  25                  30

Thr Gly Asn Thr Gly Arg Thr Pro Leu His Leu Ala Ala Trp Ala Asp
        35                  40                  45

His Leu Glu Ile Val Glu Val Leu Leu Lys His Gly Ala Asp Val Asn
    50                  55                  60

Ala Thr Gly Asn Thr Gly Arg Thr Pro Leu His Leu Ala Ala Trp Ala
65                  70                  75                  80

Asp His Leu Glu Ile Val Glu Val Leu Leu Lys His Gly Ala Asp Val
                85                  90                  95

Asn Ala Gln Asp Lys Phe Gly Lys Thr Ala Phe Asp Ile Ser Ile Asp
            100                 105                 110

Asn Gly Asn Glu Asp Leu Ala Glu Ile Leu Gln Lys Leu
        115                 120                 125

<210> SEQ ID NO 12
<211> LENGTH: 125
<212> TYPE: PRT
<213> ORGANISM: Artificial Sequence
<220> FEATURE:
<223> OTHER INFORMATION: Synthetic peptide (DARPin sequence)

<400> SEQUENCE: 12

Gly Ser Asp Leu Gly Lys Lys Leu Leu Glu Ala Ala Arg Ala Gly Gln
1               5                   10                  15

Asp Asp Glu Val Arg Ile Leu Thr Ala Asn Gly Ala Asp Val Asn Ala
            20                  25                  30

Thr Gly Asn Thr Gly Arg Thr Pro Leu His Leu Ala Ala Trp Ala Asp
        35                  40                  45

His Leu Glu Ile Val Asp Val Leu Leu Ala His Gly Ala Asp Val Asn
    50                  55                  60

Ala Ser Gly Asn Thr Gly Arg Thr Pro Leu His Leu Ala Ala Trp Ala
65                  70                  75                  80
```

```
Asp His Leu Glu Ile Val Asp Val Leu Leu Ala His Gly Ala Asp Val
            85                  90                  95

Asn Ala Ser Asp Lys Phe Gly Lys Thr Ala Phe Asp Ile Ser Ile Asp
        100                 105                 110

Asn Gly Asn Glu Asp Leu Ala Glu Ile Leu Gln Lys Leu
    115                 120                 125

<210> SEQ ID NO 13
<211> LENGTH: 141
<212> TYPE: PRT
<213> ORGANISM: Artificial Sequence
<220> FEATURE:
<223> OTHER INFORMATION: Synthetic peptide (DARPin sequence)

<400> SEQUENCE: 13

Met Lys His His His His His His Gly Ser Glu Asn Leu Tyr Phe Gln
1               5                   10                  15

Gly Ser Asp Leu Gly Lys Lys Leu Leu Glu Ala Ala Arg Ala Gly Gln
            20                  25                  30

Asp Asp Glu Val Arg Ile Leu Thr Ala Asn Gly Ala Asp Val Asn Ala
        35                  40                  45

Asn Asp Tyr Trp Gly His Thr Pro Leu His Leu Ala Ala Met Leu Gly
    50                  55                  60

His Leu Glu Ile Val Glu Val Leu Leu Lys Asn Gly Ala Asp Val Asn
65                  70                  75                  80

Ala Thr Gly Asn Thr Gly Arg Thr Pro Leu His Leu Ala Ala Trp Ala
                85                  90                  95

Asp His Leu Glu Ile Val Glu Val Leu Leu Lys His Gly Ala Asp Val
            100                 105                 110

Asn Ala Gln Asp Lys Phe Gly Lys Thr Ala Phe Asp Ile Ser Ile Asp
        115                 120                 125

Asn Gly Asn Glu Asp Leu Ala Glu Ile Leu Gln Lys Leu
    130                 135                 140

<210> SEQ ID NO 14
<211> LENGTH: 141
<212> TYPE: PRT
<213> ORGANISM: Artificial Sequence
<220> FEATURE:
<223> OTHER INFORMATION: Synthetic peptide (DARPin sequence)

<400> SEQUENCE: 14

Met Lys His His His His His His Gly Ser Glu Asn Leu Tyr Phe Gln
1               5                   10                  15

Gly Ser Asp Leu Gly Lys Lys Leu Leu Glu Ala Ala Arg Ala Gly Gln
            20                  25                  30

Asp Asp Glu Val Arg Ile Leu Thr Ala Asn Gly Ala Asp Val Asn Ala
        35                  40                  45

Asn Asp Tyr Trp Gly His Thr Pro Leu His Leu Ala Ala Met Leu Gly
    50                  55                  60

His Leu Glu Ile Val Asp Val Leu Leu Ala Asn Gly Ala Asp Val Asn
65                  70                  75                  80

Ala Ser Gly Asn Thr Gly Arg Thr Pro Leu His Leu Ala Ala Trp Ala
                85                  90                  95

Asp His Leu Glu Ile Val Asp Val Leu Leu Ala His Gly Ala Asp Val
            100                 105                 110

Asn Ala Ser Asp Lys Phe Gly Lys Thr Ala Phe Asp Ile Ser Ile Asp
```

```
                   115                 120                 125

Asn Gly Asn Glu Asp Leu Ala Glu Ile Leu Gln Lys Leu
    130                 135                 140

<210> SEQ ID NO 15
<211> LENGTH: 141
<212> TYPE: PRT
<213> ORGANISM: Artificial Sequence
<220> FEATURE:
<223> OTHER INFORMATION: Synthetic peptide (DARPin sequence)

<400> SEQUENCE: 15

Met Lys His His His His His Gly Ser Glu Asn Leu Tyr Phe Gln
1               5                   10                  15

Gly Ser Asp Leu Gly Lys Lys Leu Leu Glu Ala Ala Arg Ala Gly Gln
            20                  25                  30

Asp Asp Glu Val Arg Ile Leu Thr Ala Asn Gly Ala Asp Val Asn Ala
        35                  40                  45

Thr Gly Asn Thr Gly Arg Thr Pro Leu His Leu Ala Ala Trp Ala Asp
    50                  55                  60

His Leu Glu Ile Val Glu Val Leu Leu Lys His Gly Ala Asp Val Asn
65                  70                  75                  80

Ala Thr Gly Asn Thr Gly Arg Thr Pro Leu His Leu Ala Ala Trp Ala
                85                  90                  95

Asp His Leu Glu Ile Val Glu Val Leu Leu Lys His Gly Ala Asp Val
            100                 105                 110

Asn Ala Gln Asp Lys Phe Gly Lys Thr Ala Phe Asp Ile Ser Ile Asp
        115                 120                 125

Asn Gly Asn Glu Asp Leu Ala Glu Ile Leu Gln Lys Leu
    130                 135                 140

<210> SEQ ID NO 16
<211> LENGTH: 141
<212> TYPE: PRT
<213> ORGANISM: Artificial Sequence
<220> FEATURE:
<223> OTHER INFORMATION: Synthetic peptide (DARPin sequence)

<400> SEQUENCE: 16

Met Lys His His His His His Gly Ser Glu Asn Leu Tyr Phe Gln
1               5                   10                  15

Gly Ser Asp Leu Gly Lys Lys Leu Leu Glu Ala Ala Arg Ala Gly Gln
            20                  25                  30

Asp Asp Glu Val Arg Ile Leu Thr Ala Asn Gly Ala Asp Val Asn Ala
        35                  40                  45

Thr Gly Asn Thr Gly Arg Thr Pro Leu His Leu Ala Ala Trp Ala Asp
    50                  55                  60

His Leu Glu Ile Val Asp Val Leu Leu Ala His Gly Ala Asp Val Asn
65                  70                  75                  80

Ala Ser Gly Asn Thr Gly Arg Thr Pro Leu His Leu Ala Ala Trp Ala
                85                  90                  95

Asp His Leu Glu Ile Val Asp Val Leu Leu Ala His Gly Ala Asp Val
            100                 105                 110

Asn Ala Ser Asp Lys Phe Gly Lys Thr Ala Phe Asp Ile Ser Ile Asp
        115                 120                 125

Asn Gly Asn Glu Asp Leu Ala Glu Ile Leu Gln Lys Leu
    130                 135                 140
```

```
<210> SEQ ID NO 17
<211> LENGTH: 8
<212> TYPE: PRT
<213> ORGANISM: Artificial Sequence
<220> FEATURE:
<223> OTHER INFORMATION: Synthetic peptide (cleavage site)

<400> SEQUENCE: 17

Gly Ser Glu Asn Leu Tyr Phe Gln
1               5
```